United States Patent
Yoshikawa et al.

(10) Patent No.: US 8,092,834 B2
(45) Date of Patent: *Jan. 10, 2012

(54) COMPOSITE POWDERS AND SKIN PREPARATIONS FOR EXTERNAL USE CONTAINING THE SAME

(75) Inventors: Norinobu Yoshikawa, Yokohama (JP); Kenichi Sakuma, Yokohama (JP); Katsuki Ogawa, Yokohama (JP); Satoshi Tomomasa, Yokohama (JP); Eriko Kawai, Yokohama (JP); Hiroyuki Yokoyama, Yokohama (JP); Yukimitsu Suda, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 1655 days.

This patent is subject to a terminal disclaimer.

(21) Appl. No.: 10/481,852

(22) PCT Filed: Jun. 28, 2002

(86) PCT No.: PCT/JP02/06561
§ 371 (c)(1),
(2), (4) Date: Dec. 22, 2003

(87) PCT Pub. No.: WO03/002076
PCT Pub. Date: Jan. 9, 2003

(65) Prior Publication Data
US 2004/0175386 A1 Sep. 9, 2004

(30) Foreign Application Priority Data
Jun. 29, 2001 (JP) ................................ 2001-200002

(51) Int. Cl.
*A61K 9/14* (2006.01)
*A61K 9/18* (2006.01)

(52) U.S. Cl. ........ 424/489; 424/490; 424/401; 106/419; 106/425; 106/428; 106/431

(58) Field of Classification Search .................. 424/401, 424/489, 490; 106/419, 425, 428, 431
See application file for complete search history.

(56) References Cited

U.S. PATENT DOCUMENTS

| | | | |
|---|---|---|---|
| 4,524,787 A * | 6/1985 | Khalil et al. ................. 132/204 |
| 5,073,272 A * | 12/1991 | O'Neill et al. ................ 210/728 |
| 5,122,418 A * | 6/1992 | Nakane et al. ................ 424/401 |
| 5,439,935 A * | 8/1995 | Rawlings et al. ............. 514/451 |
| 5,545,428 A * | 8/1996 | Crimp et al. ..................... 427/8 |
| 5,616,872 A * | 4/1997 | O'Brien ........................ 73/865.5 |
| 5,786,137 A * | 7/1998 | Diamond et al. ................. 435/4 |
| 5,876,758 A * | 3/1999 | Meybeck et al. ............. 424/490 |
| 5,902,569 A * | 5/1999 | Oshima et al. .................. 424/59 |
| 5,925,350 A * | 7/1999 | Verheijen .................... 424/94.63 |
| 5,968,531 A | 10/1999 | Miyoshi et al. |
| 6,572,693 B1 * | 6/2003 | Wu et al. ........................ 106/35 |
| 6,642,252 B2 * | 11/2003 | Bisacchi et al. .............. 514/310 |
| 6,649,179 B2 * | 11/2003 | Yoshida et al. ............... 424/401 |
| 7,381,415 B2 * | 6/2008 | Yokoyama et al. ........... 424/401 |
| 2001/0014356 A1 * | 8/2001 | Yoshida et al. ............... 424/641 |

FOREIGN PATENT DOCUMENTS

| | | |
|---|---|---|
| EP | 0824086 A1 | 2/1998 |
| EP | 1112744 A1 | 7/2001 |

OTHER PUBLICATIONS

Kashimoto, A. et al. "Powder Cosmetic Material", JP 08217637, Aug. 27, 1996, English translation (PTO 10-3270).*
English Abstract for Japanese Patent Application No. 2001-010537, Publication No. 2002-212032, published Jul. 31, 2002.
English Abstract for Japanese Patent Application No. 2000-124344, Publication No. 2001-302230, published Oct. 31, 2001.
English Abstract for Japanese Patent Application No. 09-370480, Publication No. 11-193354, published Jul. 21, 1999.
English Abstract for Japanese Patent Application No. 11-123468, Publication No. 2000-319128, published Nov. 21, 2000.
English Abstract for Japanese Patent Application No. 01-322243, Publication No. 03-183620, published Aug. 9, 1991.
English Abstract for Japanese Patent Application No. 07-030690, Publication No. 08-217637, published Aug. 27, 1996.

* cited by examiner

*Primary Examiner* — Gina C Yu
(74) *Attorney, Agent, or Firm* — Rankin, Hill & Clark LLP

(57) ABSTRACT

A complex powder comprising an adsorption site and operation site,
wherein said adsorption site attracts or adsorbs a specific enzyme,
wherein said operation site inhibits or activates said enzyme,
and wherein each of the both sites are appeared on the surface of the powder.
In the complex powder described above, it is preferable that ζ-potential of the adsorption site at the pH employed is negative value,
wherein said adsorption site attracts or adsorbs the specific enzyme whose ζ-potential is positive value,
and wherein said adsorption site inhibits or activates said specific enzyme.
And it is preferable that said adsorption site has ζ-potential at pH7.5 of −10 mV or below.
In the complex powder described above, it is preferable that said specific enzyme is a plasminogen activator, and the operation site inhibits said plasminogen activator.
The complex powder described above can be used as an external composition for improving a rough skin and an external composition for a sensitive skin.

19 Claims, 15 Drawing Sheets

(A)

(B)

(C)

Zinc oxide covering quantity
0 % by weight   A

Zinc oxide covering quantity
5 % by weight   B

Zinc oxide covering quantity
10 % by weight   C

Zinc oxide covering quantity
30 % by weight   D

Mechanofusion processing

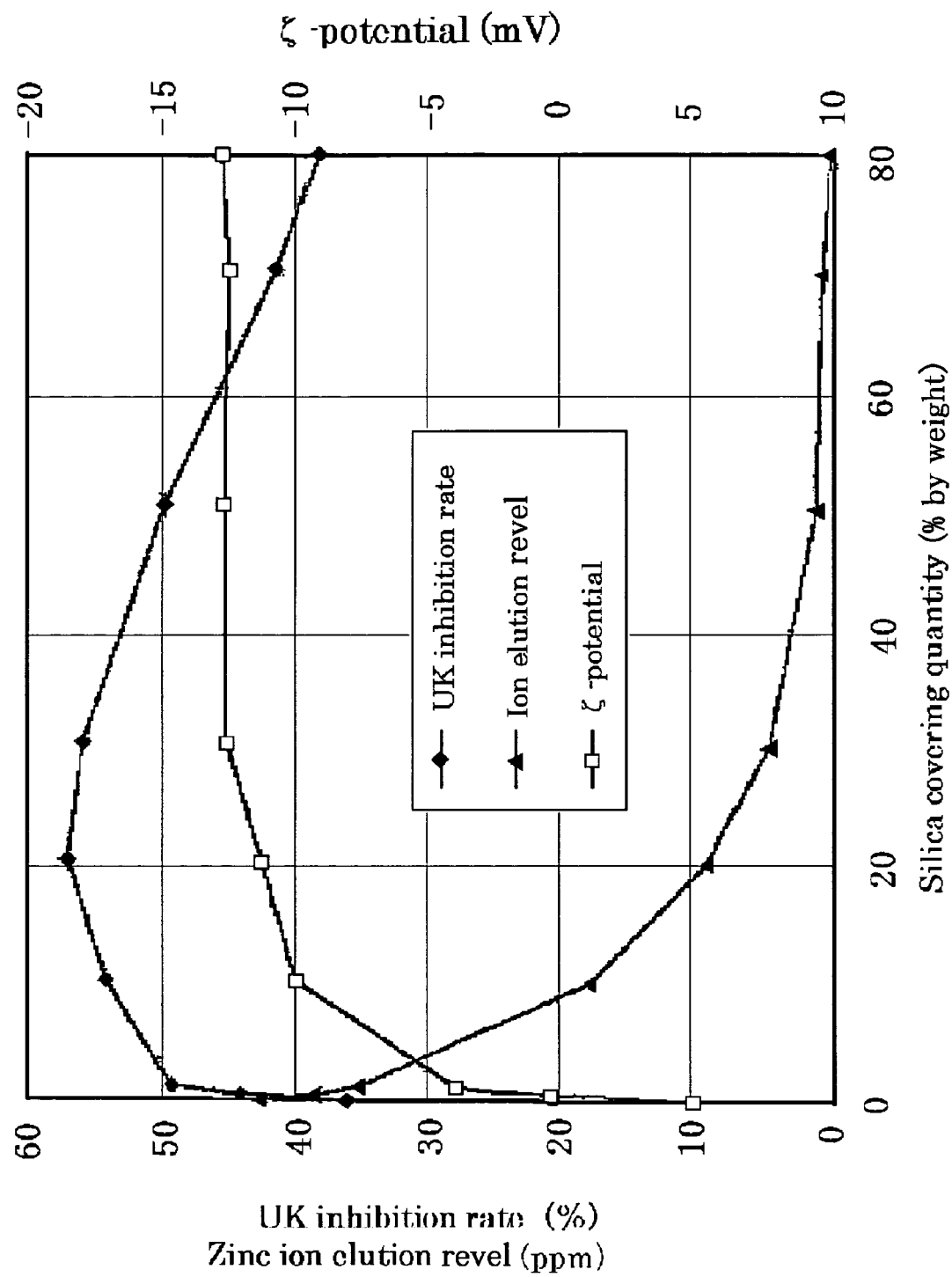

COMPOSITE POWDERS AND SKIN PREPARATIONS FOR EXTERNAL USE CONTAINING THE SAME

RELATED APPLICATIONS

This application claims priority to the Japanese Patent Application 2001-200002 filed on Jun. 29, 2001 and is hereby incorporated with reference for all purposes.

BACKGROUND OF THE INVENTION

1. Field of the Invention

The present invention relates to complex powder and external preparation for skin comprising the same, and in particular, powder that has function to living body.

2. Prior Art

It has been known that various kinds of medicines, external preparations for skin and cosmetics are effective for improvement and prevention of symptoms such as skin disease, rough skin and pimples. As an effective component of these medicines and cosmetics, for example, antiphlogistic agents, essences extracted from plants or animals which are effective for anti-inflammation, or those having moisture retaining or water retaining effect such as amino acids, polysaccharide, lipid and natural polymer have been used because these components are effective for prevention of dermatitis or prevention of water volatilization from a horny layer of epidermis.

On the other hand, an increasing attention is paid not only to morbid dermatitis such as atopic dermatitis or severe pimples but also to a condition which is not morbid dermatitis but hypersensitive reaction is shown to the change in the environment, i.e., so-called sensitive skin. Since such skin is associated frequently with an inflammation or a reduced barrier function, it may exhibit a hypersensitive reaction or irritation in response to various substances, therefore careful selection of effective components should be needed.

However, conventional medicines used as effective components for rough skin permeate into skin by percutaneous absorption, so in some cases it have probability to give other undesired effects to skin.

Accordingly, an effective component which is safe and free from irritation has been required.

SUMMARY OF THE INVENTION

An objective of the present invention is to provide a powder that has rough skin-improvement effect without percutaneous absorption, and an external composition for skin comprising the same.

As a result of diligent studies for achieving the object, the inventors found that a specific enzyme on the skin is related closely to rough skin and the like, and also that a certain complex powder adsorbs or inhibits said specific enzyme.

Thus, a complex powder of the present invention comprises an adsorption site and an operation site, wherein said adsorption site attracts or adsorbs a specific enzyme, wherein said operation site inhibits or activates said enzyme, and wherein each of the both sites are appeared on the surface of the powder.

In a complex powder described above, it is preferable that ζ-potential of the adsorption site at pH employed is a negative value, wherein said adsorption site attracts or adsorbs the specific enzyme whose ζ-potential is positive value, and wherein said adsorption site inhibits or activates said specific enzyme.

In a complex powder described above, it is preferable that said adsorption site has ζ-potential at pH7.5 of −10 mV or below.

In a complex powder described above, it is preferable that said adsorption site has ζ-potential at pH7.5 of −20 mV or below.

In a complex powder described above, it is preferable that said specific enzyme is a plasminogen activator, and wherein the operation site inhibits said plasminogen activator.

In a complex powder described above, it is preferable that inhibition rate of the plasminogen activator is 40% or higher.

In a complex powder described above, it is preferable that inhibition rate of the plasminogen activator is 45% or higher.

In a complex powder described above, it is preferable that inhibition rate of the plasminogen activator is 50% or higher, wherein said inhibition rate of the plasminogen activator is determined by measuring a decomposition activity for a synthetic substrate caused by a buffer solution comprising 0.1% of sample and 300 U/ml of a double-stranded urokinase type plasminogen activator.

In a complex powder described above, the first mode is a complex powder in which the operation site is formed in the form of stripes or spots on the surface of the adsorption site.

In a complex powder of the first mode described above, it is preferable that covering quantity of the operation site based on the adsorption site is 1 to 70% by weight.

In a complex powder of the first mode described above, it is preferable that covering rate of the operation site based on the surface of the adsorption site is 1 to 90%.

In a complex powder of the first mode described above, it is preferable that covering rate of the operation site based on the surface of the adsorption site is 2 to 70%.

In a complex powder of the first mode described above, it is preferable that covering rate of the operation site based on the surface of the adsorption site is 4 to 50%.

In a complex powder described above, the second mode is a complex powder in which the adsorption site is formed in the form of stripes or spots on the surface of the operation site.

In a complex powder described above, the third mode is a complex powder in which the adsorption site is formed in the form of a network on the surface of the operation site.

In a complex powder of the second or third modes described above, it is preferable that covering quantity of the adsorption site based on the operation site is 0.1 to 75% by weight.

In a complex powder of the second or third modes described above, it is preferable that covering quantity of the adsorption site based on the operation site is 3 to 50% by weight.

In a complex powder of the second or third modes described above, it is preferable that metal ion elution level during use is 0.7 to 40 ppm.

In a complex powder of the second or third modes described above, it is preferable that metal ion elution level during use is 1.2 to 30 ppm.

In a complex powder described above, the fourth mode is a complex powder in which the operation site and the adsorption site are formed in the form of stripes or spots on the surface of a substrate particle.

In a complex powder described above, it is preferable that the operation site is made from a metal or a metal compound capable of releasing zinc ion and the adsorption site is made from silica, talc or mica.

In a complex powder described above, it is preferable that the operation site is made from a metal or a metal compound capable of releasing zinc ion and the adsorption site is made from polyamide, polymethyl methacrylate or silicone resin.

In a complex powder described above, it is preferable that zinc ion elution level during use is 40 ppm or below.

In a complex powder described above, it is preferable that the relationship between ζ-potential and zinc ion elution level is represented by Formula (I):

$$\zeta\text{-potential (mV)} \leq \text{Zinc ion elution level (ppm)} \times 1.5 - 25 \quad \text{(I)}.$$

An external composition for improving rough skin according to the present invention comprises one or more of the complex powders described above.

An external composition for sensitive skin according to the present invention comprises one or more of the complex powders described above.

In an external composition for improving rough skin described above, it is preferable that one or more selected from a group consisting of a zinc oxide-covering silica, zinc oxide-covering talk and zinc oxide-covering mica are contained.

In an external composition for sensitive skin described above, it is preferable that one or more selected from a group consisting of a zinc oxide-covering silica, zinc oxide-covering talk and zinc oxide-covering mica are contained.

The complex powder described above can be used as an improving agent for rough skin.

The complex powder described above can be used as a care agent for sensitive skin.

BRIEF DESCRIPTION OF THE DRAWINGS

FIG. 1A represents a complex powder an operation site is formed as stripes or spots on adsorption site; FIG. 1B represents a complex powder an adsorption site is formed as stripes or spots on operation site; FIG. 1C represents a complex powder an adsorption site is formed as a network on the entire surface of an operation site; FIG. 1D represents a complex powder an operation site and an adsorption site are supported on, coated on, included in, adsorbed on or mixed in a substrate particle; FIG. 1E represents a complex powder an operation site such as zinc ion is supported in between the layers of an adsorption site such as laminar clay mineral.

FIG. 2A depicts a urokinase (UK)-type plasminogen activator having only a ZnO operation site. FIG. 2B depicts a complex powder having both a zinc oxide operation site and a silica adsorption site where the adsorption site forms a network on the operation site. FIG. 2C depicts a complex powder having a zinc oxide operation site in the form of spots on the absorption site.

FIG. 15 shows the relation between silica covering quantity and UK inhibition rate, the relation between silica covering quantity and ζ-potential, and the relation between silica covering quantity and zinc ion elution level in a zinc oxide covered silica complex powder of Embodiment 9.

DETAILED DESCRIPTION OF THE PREFERRED EMBODIMENT

The complex powder and the external preparation for skin comprising the same according to this invention were found out by the circumstances like the following.

It has been made clear recently that an activity change of protease, especially an activity change of fibrinogenolysis type enzyme (plasminogen activating enzyme) such as plasmin or plasminogen activator, is closely related to a formation of various types of diseased skin accompanied with rough skin or abnormal cornification.

For example, it was reported that a distribution of plasmin in an epidermal cell layer of rough skin experimentally formed was changed relative to a distribution of plasmin in epidermal cell layer of normal skin, and anti-plasmin agent is effective for improvement and prevention of rough skin (Kenji Kitamura: J. Soc. Cosmet. Chem. Jpn; 29(2), 1995). Further in case of atopic dermatitis high fibrinogenolysis activity in epidermis was also reported (T. Lotti: Department of Dermatology; 28(7), 1989). On the other hand, in the case of psoriasis, representative of diseased skin accompanied with inflammation and abnormal cornification, it was reported that there exists high plasminogen activator activity at a portion of parakeratosis in an epidermis of the affected part (Haustein: Arch. Klin. Exp. Dermatol; 234, 1969), and it was also reported that a plasminogen activator was extracted from a flake of psoriasis by using a high-concentration buffer solution(Fraki, Hopsu: Arch. Dermatol. Res; 256, 1976).

A plasminogen activator is a protease which selectively acts on a plasminogen, (a precursor of plasmin) and transform plasminogen to active form. Based on the above-mentioned existing background, the present inventors paid attention to the behavior of the various kinds of enzymes on the skin on the occasion of the development of a new medicine for rough skin. Then various kinds of inorganic powder were investigated for improvement and prevention of rough skin, based on the idea that a material which adsorbs and deactivates a plasminogen activator at a surface of skin and does not have the process of percutaneous absorption would be effective for improvement and prevention of diseased skin or rough skin which accompanies an activity change for a plasminogen activating enzyme, and also would be highly safe for human body. As a result of exploring various kinds of powder, it was found that a specified complex powder adsorbs and inhibits plasminogen activator.

Structure of Complex Powder

Figure 1:
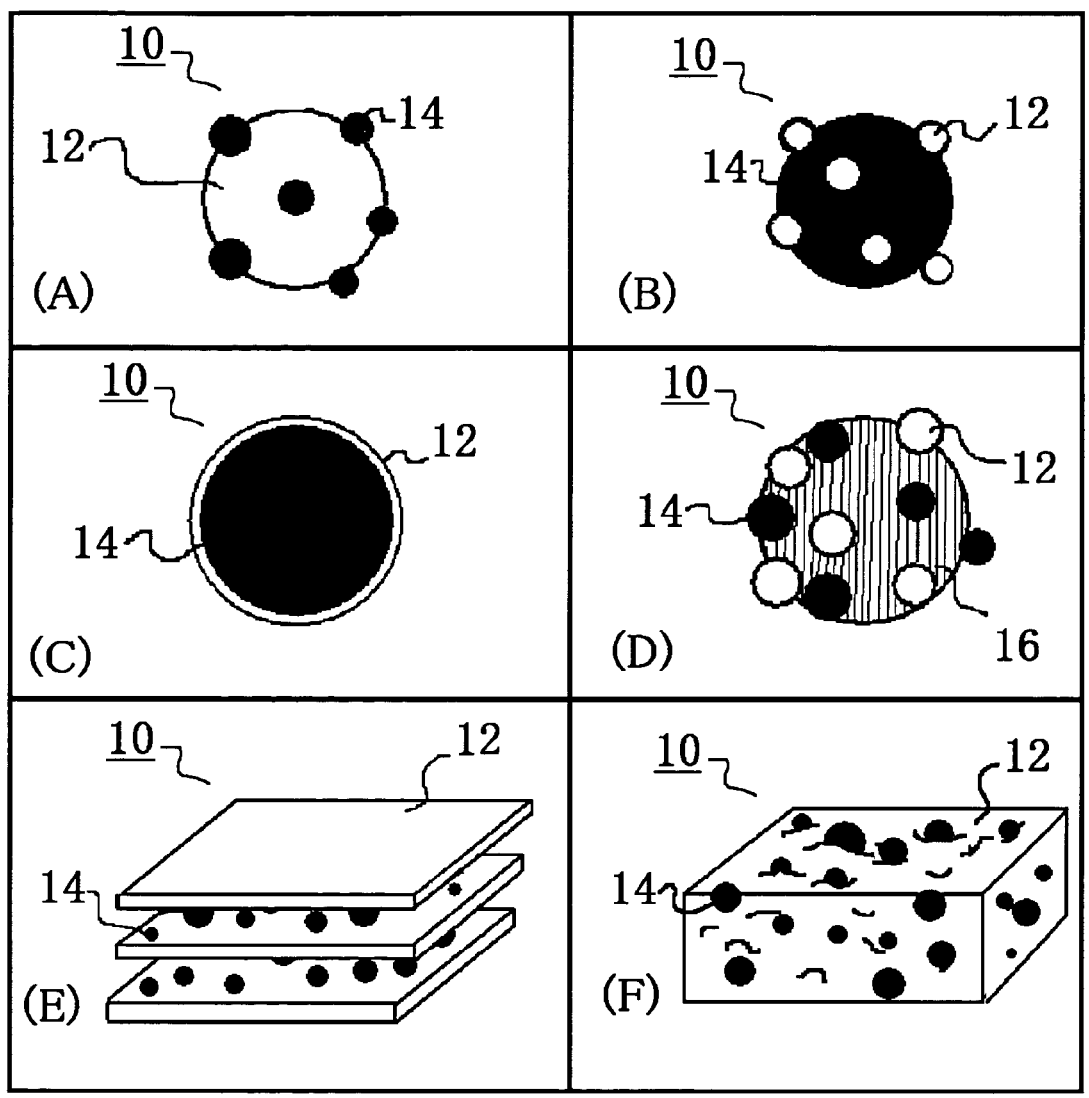
FIGS. 1A-1E schematically represent the constitution of the complex powder of this invention.
FIG. 1F represents a complex powder in which an operation site such as zinc oxide is included in an adsorption site of a porous tabular silicon oxide or in which an adsorption site is included in an operation. In the figures, 10 represents a complex powder; 12 represents an adsorption site; 14 represents an operation site; and 16 represents a substrate particle.

A complex powder 10 of this invention, typically as shown in FIG. 1(A), has an operation site 14 formed as stripes or spots on a powder 12 with an ability of adsorbing an enzyme (adsorption site).

Also as shown in FIG. 1(B), an adsorption site 12 which attracts or adsorbs an enzyme is formed as stripes or spots on a powder 14 with an ability of inhibiting or activating the enzyme (operation site).

Alternatively, as shown in FIG. 1(C), an absorption site 12 is formed as a network on the entire surface of a powder 14 with an ability of activation (operation site).

Those which can also be illustrated as a complex powder 10 of this invention are;

A complex powder 10 in which an operation site 14 and an adsorption site 12 are supported on, coated on, included in, adsorbed on or mixed in a substrate particle (FIG. 1(D));

A complex powder 10 in which an operation site 14 such as zinc ion is supported between the layers of an adsorption site 12 such as laminar clay mineral (FIG. 1(E)); and A complex powder 10 in which an operation site 14 such as zinc oxide is included in an adsorption site 12 of a porous tabular silicon oxide (FIG. 1(F)) (or a complex powder in which an adsorption site is included in an operation site).

In the case of FIG. 1(A), it is preferable to adjust the covering quantity and the covering rate in order to form an operation site in such a manner that the operation effect at the operation site can sufficiently be exerted and the absorption effect at an adsorption site is not interfered. A preferred covering quantity at the operation site is 1 to 70% by weight based on the adsorption site, and a preferred covering rate at the operation site is 1 to 90%, more preferably 2 to 70%, especially 4 to 50% based on the surface area of the adsorption site.

In the case of FIG. 1(B) or (C), it is preferable to adjust the covering quantity and the covering rate in order to form an absorption site in such a manner that the absorption effect at the absorption site can sufficiently be exerted and the operation effect at an operation site is not interfered. A preferred covering quantity at the adsorption site is 0.1 to 75% by weight based on the operation site.

Also in the cases of FIGS. 1(D), (E) and (F), it is preferred to form a structure in such a manner that the operation effect at the operation site can be sufficiently exerted and the absorption effect at an adsorption site is not interfered.

For example the complex powder shown in FIG. 1(D) is manufactured as follows; polyethylene powder, silica and zinc oxide are premixed and the silica and the zinc oxide are covered on the surface of the polyethene powder by mechanofusion processing. The mechanofusion processing is described in detail later.

Adsorption Site

In the complex powder of the present invention, an adsorption site is selected in relation with the target enzyme to be adsorbed. It is preferable to be evaluated on the basis of the correlation with $\zeta$-potential of the target enzyme.

When a powder has an electric charge in liquid, an ion with the opposite electric charge is attracted to said powder by static electricity power in order to compensate the electric charge, so an electric double layer is produced. The outermost potential of the double layer is $\zeta$-potential. Accordingly, the $\zeta$-potential is employed preferably in evaluating the surface charge condition of an object, enabling the evaluation of an ability of adsorbing an enzyme electrically.

The $\zeta$-potential can be obtained in accordance with the Smoluchowski's formula: $\zeta\text{-potential}=4\pi\eta U/\in$ (in the above formula, $\eta$ is the viscosity of the solvent, U is the electrophoresis mobility, $\in$ is the dielectric constant of the solvent).

In order to obtain $\zeta$-potential, an electrophoresis is employed to measure the velocity of the colloidal particle (V) and the electrophoresis mobility (U). Under the electric field (E), the charged colloidal particle moves. V is obtained by the formula: $V=L/t$ (wherein L is the distance of the movement and t is the time), and U is obtained by the formula: $U=V/E$.

When the target enzyme is a plasminogen activator whose $\zeta$-potential is positive value, $\zeta$-potential of the substance forming an adsorption site is preferably negative value at pH employed. The $\zeta$-potential of the substance forming an adsorption site is preferably −10 mV or below at pH 7.5, more preferably −20 mV or below.

The method for measuring $\zeta$-potential is discussed later.

The relationship between $\zeta$-potentials of major substances at pH 7.5 and adsorption rate of UK at 100 ppm is shown in Table 1.

TABLE 1

| Sample | $\zeta$-potential (mV) | UK adsorption rate (%) |
|---|---|---|
| Inorganic powder | | |
| Silica(Sunsphere L ™) | −20.0 | 82 |
| Mica (Eightpearl 300S ™) | −18.9 | 79 |
| Talc (Talk JA-68R ™) | −19.3 | 78 |
| Zinc oxide (manufactured by Seido chemical industry Co. Inc.) | +5.5 | 29 |
| Alumina (Maxlight A100 ™) | +17.3 | 0 |
| Organic powder | | |
| Polyamide (Nylon SP500 ™) | −32.0 | 34 |
| Polymethyl methacrylate (Ganzpearl ™) | −18.0 | 42 |
| Silicone resin (Tospearl 145A ™) | −14.0 | 30 |
| Ethyl carbamate (Plastic powder ™) | −13.0 | 27 |
| Organo polysiloxane extremer spherical powder (Trefil E506S ™) | −12.0 | 18 |
| Cellulose (Celluflow C-25 ™) | −2.0 | 21 |
| Polyethylene (Flo-thene UF ™) | +1.0 | 10 |

The method for measuring UK adsorption rate is discussed later in detail.

As shown in Table 1, lower $\zeta$-potential tended to result in a higher UK adsorption rate over respective organic powders and inorganic powders, indicating a correlation between ζ-potential and UK adsorption rate.

A preferable material for an adsorption site may be inorganic powders such as silica, mica, talc and the like and organic powders such as polyamide, polymethyl methacrylate, silicone resin and the like.

Operation Site

An operation site is also selected in relation with an enzyme to be targeted.

In the case that the target enzyme is plasminogen activator, metals or metal compounds that releases ions of the Groups IV, IX, X, XI and XII are raised as an operation site. A particularly preferred metal ion may for example be zinc ion.

The metal compounds releasing the metal ions may for example be inorganic compounds such as oxides, hydroxides, nitrates, chlorides, hydroxides, carbonate, bicarbonates, sulfates, borates, persulfates as they are and as being contained in molecules of inorganic compounds (complexes):

organic acid salts such as glycerophosphate, acetates, hydroxides, α-hydroxy acid salts (citrates, tartrates, lactates, malates), fruit acids, amino acid salts (aspartates, alginates, glycolates, fumarates), fatty acid salts (palmitates, oleates, caseinates, behenates) and the like. When a complex powder of this invention is used in an external composition, an especially preferred metal compound may for example be zinc oxide.

The followings are UK inhibition rates of various ions at the ion concentration of 100 ppm.

TABLE 2

| Sample | UK active inhibition rate (%) |
| --- | --- |
| $Zn^{2+}$ | 52 |
| $Zr^{4+}$ | 45 |
| $Cu^{2+}$ | 36 |
| $Ni^{2+}$ | 30 |
| $Co^{2+}$ | 27 |
| $Al^{3+}$ | 16 |
| $Ce^{3+}$ | 5 |
| $Na^+, Li^+, K^+, Mn^{2+}, Ba^{2+}, Mg^{2+}, Ba^{2+}, Ca^{2+}$ | 0 |

The method for measuring UK inhibition rate is detailed later.

As shown in Table 2, zinc ion exhibited the most excellent UK inhibiting effect. While an analogous UK inhibiting effect was exhibited by the zirconium ion, there were the ions not exhibiting substantially UK inhibiting effect such as sodium ion and calcium ion. Accordingly, it is admitted that there is high specificity in the operation of each ion to the enzyme.

Zinc oxide has been mainly used as an external composition like cosmetics, or ultraviolet-scattering agent and as a white pigment. However its ultraviolet-scattering effect was not sufficient, and zinc oxide decreased stability of a formulation by its catalytic activity. Based on these problems, for the purpose of improvement of stability and utility of a formulation system without decreasing the ultraviolet-scattering function, zinc oxide which has more smaller particle size than that of previously used zinc oxide (Japanese Patent Publication No. Shou 60-33766, Japanese Patent Publication No. Hei 5-77644) or a complex with various inorganic or organic compounds have been developed (Japanese Patent Laid Open No. Hei 1-190625, Japanese Patent Laid Open No. Hei 3-183620, Japanese Patent Laid Open No. Hei 7-277914, Japanese Patent Laid Open No. Hei 10-87434, Japanese Patent Laid Open No. Hei 10-87467, Japanese Patent Laid Open No. Hei 10-87468).

On the other hand, zinc oxide is registered in Japanese pharmaceutical codex, and is known to combine with protein existing on skin to form film and as a result having a pharmacological effect such as astriction, improvement of inflammation and protecting. Based on these pharmacological effects, zinc oxide has been used as a form of a mixture of zinc oxide, lanolin and white ointment or as a powder preparation mixed with those such as talc or starch for applying to diseased skin, rough skin by diaper and so on. Moreover, to add medical effect of zinc oxide to other materials, zinc oxide was applied to skin as a form of mixture with other agents such as an anti-inflammating agent, antibacterial material (Japanese Patent Publication No. Hei 4-63046, Japanese Patent Publication No. Hei 6-76330, Japanese Patent Laid Open No. Hei 2-23361, Japanese Patent Laid Open No. Hei 6-157277, Japanese Patent Laid Open No. Hei 8-217616, Japanese Patent Laid Open No. Shou 57-62220), anti-oxidation agent (Japanese Patent Laid Open No. Hei 7-304665) and protease inhibitor (Japanese Patent Laid Open No. Hei 3-169822), or as a form of a complex.

However, a report or a description rarely exists concerning the character of zinc oxide suitable for medicine. Such a description only exists in Japanese patent laid open No. Hei 6-239728 where it is described that ultra-microparticle zinc oxide is more effective on astringent than zinc oxide previously used, but a concrete example is not described in that literature.

Substrate Particle

As mentioned above, a complex powder of the present invention may have a structure in which an operation site and an absorption site are formed in stripes or spots on the surface of a substrate particle. Said substrate particle is not limited particularly as long as it does not affect the effect of the present invention, and may for example be an inorganic substrate particle, organic substrate particle, inorganic pigment substrate particle, inorganic pigment substrate particle and the like.

Complex Effect

In a complex powder of the present invention, the effect of an operation site to a specific enzyme is further improved due to the presence of an adsorption site of said enzyme.

Figure 2:
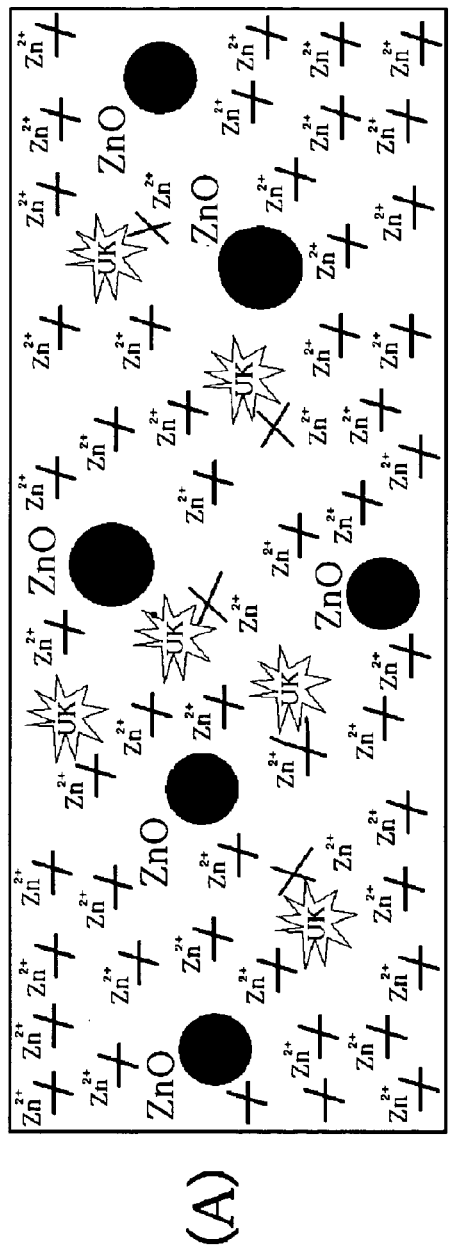
FIGS. 2A-2C schematically represent the active inhibition operation of the complex powder that is linked to this invention. In particular.
Figure 2:
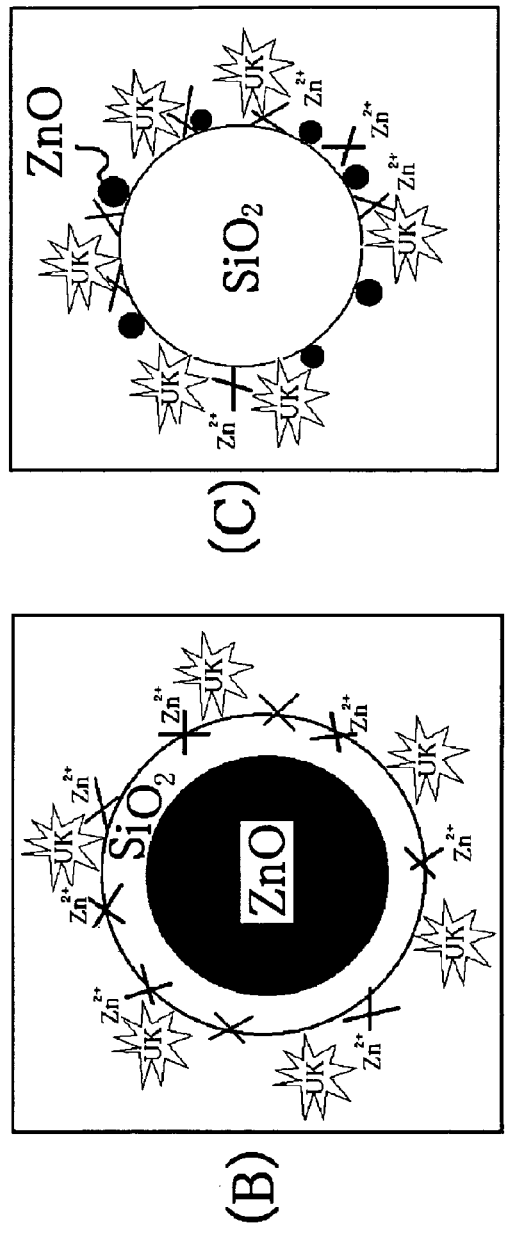

FIG. 2 shows the diagram indicating the inhibition of double-stranded urokinase (UK)-type plasminogen activator. As shown in FIG. 2(A), when only an operation site is present, a sufficient inhibition of the UK requires high concentration of the zinc ion, which is not suitable to incorporate an external composition from the pharmaceutical point of view.

Nevertheless, in the cases of a complex powder having the both of an operation site and an absorption site, such as the case using zinc oxide as an operation site and silica as an adsorption site where the adsorption site is formed as a network on the operation site (FIG. 2(B)) or where the operation site is formed as spots on the adsorption site (FIG. 2(C)), the operation site readily act on the UK because of the adsorption of the UK by the adsorption site, whereby allowing the UK activity inhibiting effect to be exerted effectively even at a low zinc ion concentration.

Even when an absorption site and an operation site are simply mixed, the effect may sometimes be higher than those of the respective sites used independently. Nevertheless, an extremely high operation to the enzyme, such as a plasminogen activator inhibiting effect, is exhibited particularly by a complex powder which has the operation site and the adsorption site are to be a complex on the surface of said complex powder.

The present inventors tested trypsin as a reference which is classified into a serine protease as same as a plasminogen activator. In the case of the trypsin, the trypsin was adsorbed on complex powder, but its activity was maintained as same as before adsorption. So it should be obvious that it cannot be said that complex powder usually inhibits enzyme activity.

For the purpose of improvement of properties such as ultraviolet scattering effect, safety, stability and usability, a complex powder has been developed which has a particle component composed of zinc oxide and a material that covers zinc oxide or is covered by zinc oxide, such as inorganic or organic compounds such as carbonate, sulfate (Japanese Patent Laid Open No. Hei 10-87468), meta-magnesium silicate aluminate (Japanese Patent Laid Open No. Hei 1-308819), silica, alumina (Japanese Patent Laid Open No. Hei 3-183620, Japanese Patent Laid Open No. Hei 10-87467), organofluorinated modified silicone (Japanese Patent Laid Open No. Hei 7-277914), polyester, nylon and cellulose (Japanese Patent No. 2628058). However there is not the report that zinc oxide adsorbs the enzyme on the skin and operate to the activity of said enzyme, in as long as this inventor knows. Although a fluorescent zinc oxide manufactured by calcinating of zinc oxide under reduction-atmosphere with hydrogen or carbon monoxide (disclosed in Japanese Patent Laid Open No. Hei 5-117127) was tested, it showed little adsorption of a plasminogen activator and little inhibition of its activity, and also did not show any improvement of skin.

The complex powder of the present invention is employed preferably to skin having pathological dermatitis or to sensitive skin, due to the ability of reducing the irritation.

When complex powder of the present invention is used as an external preparation for skin, it can be treated with materials like silicone for giving hydrophobic property on its surface if needed.

An external preparation for skin of the present invention can comprise one or more types of complex powders mentioned above and gives excellent effect on adsorption of plasminogen activator and inhibition of its activity, improvement of skin results, and it is very safe.

Two kinds of plasminogen activator are known. One is called urokinase and exists in healthy epidermis and the other is called organized plasminogen activator and exists in morbid skin.

Complex powder of the present invention has an effect for both types of plasminogen activator mentioned above. The effect is on adsorption of plasminogen activator and on inhibition of plasminogen activity.

The preferable blending amount of complex powder in an external preparation for skin of the present invention is 0.1 to 50.0% by weight per total amount, more preferably 2.0 to 20.0% by weight per total amount, and the most preferably 5.0 to 20.0% by weight per total amount. When used with less than 0.1% by weight the effect of the present invention is not sufficient, and when used with more than 50.0% by weight it is difficult to formulate an external preparation for skin.

If the effect of the present invention is maintained, an external preparation for skin of the present invention can include components usually applicable to an external preparation for skin used as cosmetics or medicines, such as moisture retaining agents, oil ingredients, ultraviolet absorbent, emulsifiers, surfactants, thickeners, alcohols, powder components, colorants, hydrophilic components, water, skin eutrophic medicine.

Further an external preparation for skin of the present invention can comprise: a sequestering agent such as disodium EDTA, trisodium EDTA, sodium citrate, sodium polyphosphate, sodium metaphosphate, gluconic acid and malic acid: plant extracts such as glycyrrhiza extract, Chinese quince extract, ichiyakusou extract: medical components such as caffeine, tannin, verapamil, tranexamic acid and its derivatives, tocopherol acetate, glycyrrhezinic acid and its derivatives or salts: whitening agents such as vitamin C, magnesium ascorbate phosphate, glucoside ascorbate, arbutin, kojic acid: amino acids and its derivatives such as arginine, lysine: saccharides such as fructose, mannose, erythritol, trehalose, xylitol: and so on.

An external preparation for skin of the present invention can be applied in a form such as ointment, cream, lotion, pack, foundation, face powder, cheek, eye shadow, sun screen, lipstick, bath composition, paper for oil absorption, paper powder and other forms normally used for external for skin preparations. A shape of said external preparation for skin is arbitrary.

A complex powder of this invention exhibits an excellent effect especially on skin such as sensitive skin suffering from difficulty in using cosmetics of prior arts.

A sensitive skin is defined in publications as follows:

"A skin usually susceptible to a damage due to a specific response to quasi-drugs, cosmetics, plants, ultraviolet ray, metals to which most of human beings do not respond particularly."

"A skin which is sensitive constitutionally to an allergenic substances (pollen, fragrance) or irritative substances (alcohols) due to a reduced barrier function of skin."

"A skin susceptible to a damage by an irritating substance only temporarily when the resistance of skin or the physiological functions of skin are deteriorated due to an insufficient sleep, overwork, menstruation, seasons change, mental stress and the like."

"A skin posing an anxiety about the use of cosmetics used routinely."

Thus, factors for sensitive skin condition are reduced skin barrier function, reduced skin irritation threshold, skin dryness, substance causing contact dermatitis, physicochemical irritation, stress, physical condition, seasons change, ultraviolet ray, menstruation and the like. It is also possible that one's false skin care itself causes a sensitive skin and that one's obsession just causes sensitive skin.

As used herein, a subject having a sensitive skin is defined as one who experiences abnormal felling in any of the procedures (1) to (5) shown below.

(1) 100 μl of 5% aqueous solution of citric acid is applied over the cheek and allowed to stand for 10 minutes.

(2) 100 μl of 5% aqueous solution of lactic acid is applied over the cheek and allowed to stand for 10 minutes.

(3) 100 μl of 50% ethanol solution is applied over the cheek and allowed to stand for 10 minutes.

(4) An unwoven fabric (2×2 cm) is impregnated with 100 μl of 0.2% aqueous solution of methylparaben, and allowed to stand on the cheek for 10 minutes.

(5) An unwoven fabric (2×2 cm) is impregnated with 100 μl of 5% aqueous solution of SDS, and allowed to stand on the cheek for 10 minutes.

The abnormal felling means relatively painful feeling experienced on skin, such as stingy pain, irritating sensation, itching sensation, burning sensation, discomfort, pricking pain and the like.

In the following, the present invention will be explained by using specific examples. However, the present invention should not be restricted thereto. Unless otherwise stated, quantities are expressed as percent by weight.

First of all, concrete methods for testing the plasminogen activator adsorbing effect, the plasminogen activator inhibiting effect and skin improving effect are discussed below.

1. Plasminogen Activator Adsorption/Inhibition Operation Test (In Vitro)

(1) Preparation of the Samples

Talc, mica, silica, complex powder of the example, and zinc oxide of the comparative were used as samples. 0.1% of a sample was suspended in water and the adsorption/activation inhibiting effect to urokinase (UK) was evaluated.

(2) Measurement of Adsorbing Effect for Plasminogen Activator (Measuring Method of the UK Adsorption Rate)

Tris-HCl buffer (pH 7.4) was added into 20 µl of a sample suspension to give total amount of 180 µl, followed addition of 20 µl of a precursor type urokinase containing solution (10 µg/ml). The solution was left for 5 minutes at room temperature, and the sample powder was filtered and the filtrate was collected. The sample powder was washed sufficiently with a constant amount of Tris-HCl buffer, and the Tris-HCl buffer used for washing was added to the filtrate, and this solution was used as the non-adsorbent urokinase containing solution. The concentration of said non-adsorbent urokinase containing solution was determined by the ELISA method using TintElize uPA(biopool), and then the amount of the urokinase adsorbed on the sample powder was calculated.

(3) Measurement of Activation Inhibiting Effect for a Plasminogen Activator (Measuring Method of the UK Active Inhibition Rate)

Tris-HCl buffer(pH 7.5) was added in 20 µl of a sample suspension to give the total amount of 180 µl, following addition of 20 µl of an activator type urokinase containing solution (300 U/ml). The solution was left for 30 minutes at the room temperature, and 20 µl of S2444 (CHROMOGENIX), specified synthetic substrate of urokinase, was added to the solution, and the solution was left for 30 minutes at 37° C. Then the reaction was stopped by adding 20 µl of water solution containing 12% of trichloroacetic acid, then the sample powder was filtered and activity of urokinase was derived by measuring absorbance of the filtrate at 405 nm, then activation inhibition rate of a plasminogen activator was calculated.

2. Test for Evaluating the Rough Skin Preventing Effect (In Vivo)

(1) Preparation of the Samples

As same as the test procedure at the condition in vitro, talc, mica, silica, complex powder of the example, and zinc oxide of the comparative were selected as samples and a sample suspension was prepared by suspending 3% of a sample powder in water. Then the rough skin preventing effect caused by zinc oxide of the present invention was evaluated.

(2) Judgment of the Rough Skin Preventing Effect

A cotton sheet (2×2 cm) soaked by 5% of SDS solution was put on inside of each forearm of panelists composed of 54 men and left alone for 15 minutes. The forearm of a panelist was washed, and then 0.5 ml of a sample suspension selected for each panelist was applied on the portion where said cotton sheet was put, and 0.5 ml of water was also applied as a reference on the portion where said cotton sheet was put and the sample suspension was not applied (n=3). This procedure, applying the sample and water, was daily repeated for seven days. After seven days past, the tested portion was sufficiently washed, and left for 60 minutes, then a condition of rough skin caused by SDS was observed and the evaluation point was decided based on the judgment standard described below. The difference of the evaluation point between the sample applied portion and the reference portion was derived for each panelist, and the differences derived were summed for each sample, and the rough skin preventing effect of each sample was judged based on the judgment standard described below.

<The Standard Used to Decide the Evaluation Point Concerning the Condition of Rough Skin>

Evaluation Point 4:
An obvious erythema and/or scaled horny layer was observed.
Evaluation Point 3:
A medium erythema and/or a little degree of scaled horny layer was observed.
Evaluation Point 2:
A little erythema and/or a crack in horny layer was observed.
Evaluation Point 1:
The surface of horny layer looks white, or looks like powder-attached.
Evaluation Point 0:
No symptom was observed.

<The Judgment Standard for the Rough Skin Preventing Effect>

AA (Obvious effect was recognized):
The difference of the evaluation point is more than 6.
A (A little effect was recognized):
The difference of the evaluation point is 4 or 5.
B (A trend of prevention was recognized):
The difference of the evaluation point is 2 or 3.
C (No effect was recognized):
The difference of the evaluation point is less than 1.

3. Method for Measuring ζ-potential

A sample was dispersed in Tris-HCl buffer solution at pH 7.5, treated ultrasonically, and then measured. The ζ-potential was measured using an electrophoresis scattering photometer LEZA-600 manufactured by Otsuka Electronics Co., Ltd. Each sample was measured 3 times and the mean value of the results was represented.

Zinc Oxide Concentration and UK Active Inhibition Rate

The relationship between the concentration and the UK inhibition rate was examined about the zinc ion, which exhibits a plasminogen activator inhibiting effect. The UK inhibition rate was measured by the method described above.

TABLE 3

| Zinc ion concentration (ppm) | UK active inhibition rate (%) |
|---|---|
| 0.1 | 3 |
| 1 | 4 |
| 10 | 21 |
| 40 | 30 |
| 45 | 40 |
| 50 | 50 |
| 100 | 52 |
| 1000 | 74 |

As evident from Table 3, a higher zinc ion concentration gave a higher inhibition rate. An UK inhibition rate of 40% or higher required a zinc ion concentration of 45 ppm or higher, and an UK inhibition rate of 50% or higher required a zinc ion concentration of 50 ppm or higher.

However, the presence of the zinc ion at a higher concentration may not be preferable in view of the preparation of a pharmaceutical, and the zinc ion concentration is preferably 40 ppm or lower.

Zinc Ion Elution Level and UK Active Inhibition Rate

Then the zinc ion elution levels from any of various zinc oxides on the market and a silica-covering zinc oxide as an complex powder of the present invention (silica covering quantity: 20% by weight) were measured and the relationship with the UK inhibition rate were investigated.

A dispersion of each sample in a 0.01 Tris-HCl buffer (pH 7.5) was stirred, centrifuged, and the filtrate was subjected to an ICP analysis to measure the zinc ion elution level of each sample. In accordance with the method for measuring the UK inhibition rate described above, the UK inhibition rate of each sample suspension was calculated.

TABLE 4

| Sample | Zinc ion elution Quantity (ppm) | UK active inhibition rate(%) |
|---|---|---|
| Silica covering zinc oxide | 8.9 | 49 |
| Zinc oxide A on the market | 42.5 | 37 |
| Zinc oxide B on the market | 47.9 | 30 |
| Zinc oxide C on the market | 47.1 | 33 |
| Zinc oxide D on the market | 43.5 | 26 |
| Zinc oxide E on the market | 50.5 | 45 |
| Zinc oxide F on the market | 47.9 | 41 |

As evident from Table 4, there was almost no difference in the zinc ion elution level among various zinc oxides on the market, whose levels were around 45 ppm.

Accordingly, there was almost no difference in the UK inhibition rate among the zinc oxides on the market, whose values were around 40%. These results were in agreement with the relationship between the zinc ion concentration and the UK inhibition rate shown in Table 3. Accordingly, the inhibition of the activity by the ion oxide alone may be attributable to the eluted zinc ion.

Nevertheless, the dispersion of the silica-covering zinc oxide (complex powder of the present invention) exhibited 45% UK inhibition in spite of its low zinc ion elution level 8.9 ppm, and this fact is not in agreement with the relationship between the zinc ion concentration and the UK inhibition rate shown in Table 3. Thus, it was suggested that the UK activity inhibition by the silica-covering zinc oxide is not attributable only to the eluted zinc ion.

Figure 3:
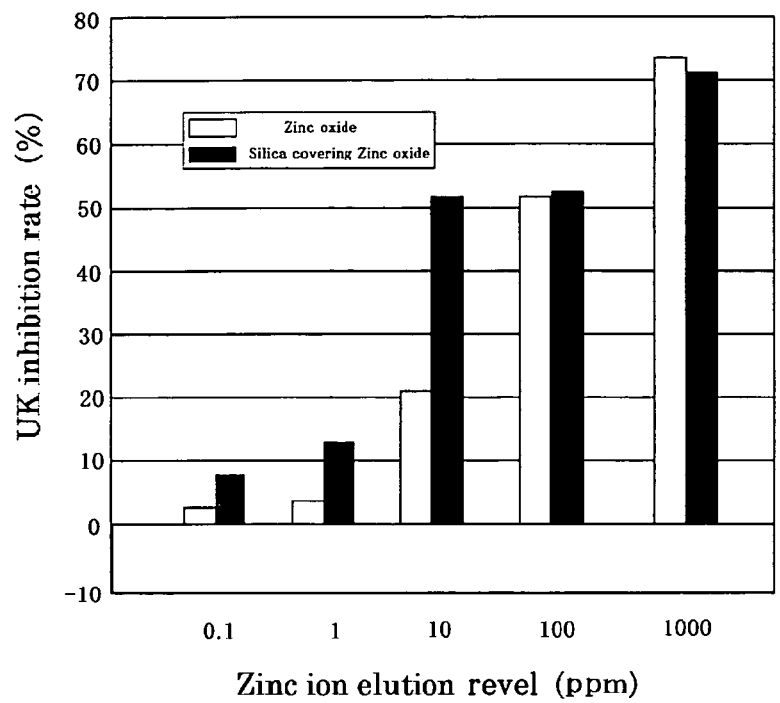
FIG. 3 graphically shows the relation between zinc ion elution level and UK inhibition rate of the complex powder. In particular, the upper graph shows the relation between UK inhibition rate and zinc ion elution level for zinc oxide as compared to a zinc oxide coated with silica, and the lower graph shows the relation between UK inhibition rate and zinc ion elution level for zinc oxide as compared to a zinc oxide coated with alumina, the procedure outlined in Example (3), Measurement of activation inhibiting effect for a plasminogen activator.
Figure 3:
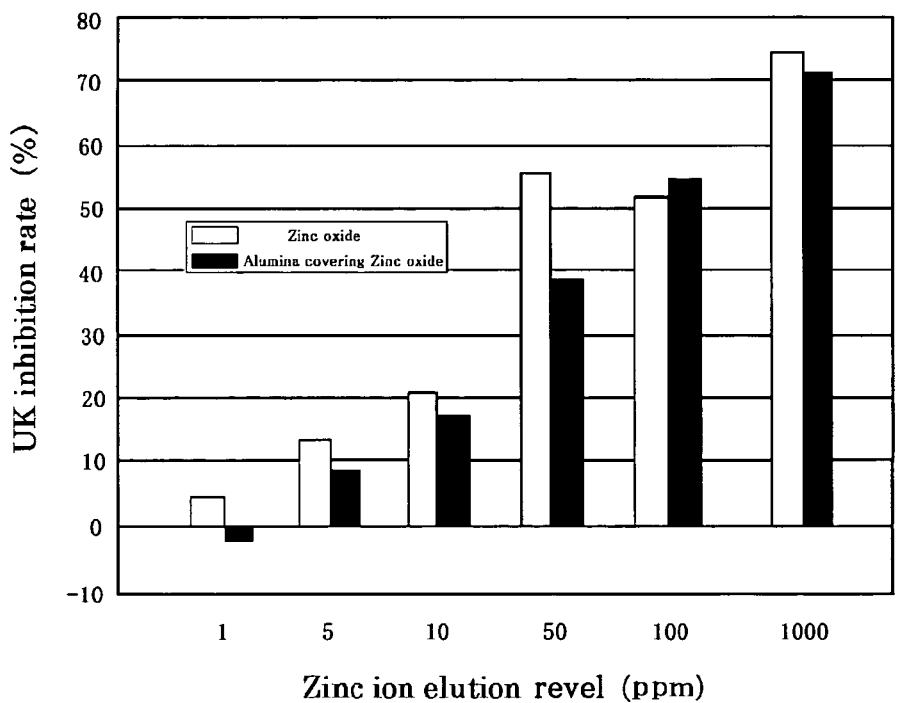

Accordingly, the zinc ion elution level and the UK inhibition rate of a zinc oxide, silica-covering zinc oxide and alumina-covering zinc oxide were measured by the method described above, and the relationship between the zinc ion elution level and the UK inhibition rate was investigated. The results are shown in FIG. 3.

Silica (ζ-potential: −20.0 mV, UK adsorption rate: 82%)
Alumina (ζ-potential: +17.3 mV, UK adsorption rate: 0%)

The alumina-covering zinc oxide using an alumina(ζ-potential: +17.3 mV) exhibited a lower UK inhibition rate compared with the zinc oxide, while the silica-covering zinc oxide using a silica(ζ-potential: −20 mV) exhibited a higher UK inhibition rate compared with the zinc oxide even at a lower zinc elution level.

These findings may be due to an efficient inhibition of the UK activity by the zinc ion as a result of the zinc ion and the UK were adsorbed onto the surface of the silica, since the ζ-potential of the silica is negative.

The fact that the silica-covering zinc oxide exhibited a high UK inhibition rate in spite of a low zinc ion concentration of the solution may possibly be due to the UK activity inhibition by the silica-covering zinc oxide which is attributable not only to the eluted zinc ion but also to the UK absorption effect of the silica. The presence of the zinc ion at a high concentration may not be preferable in view of the preparation of a pharmaceutical such as an external composition. A complex powder of this invention is preferred since it exhibits a UK inhibiting effect even at a low concentration of the zinc ion.

(A) Complex Powder Having Operation Site on Absorption Site (Zinc Oxide-Covering Powder)

Embodiment 1

Figure 4:
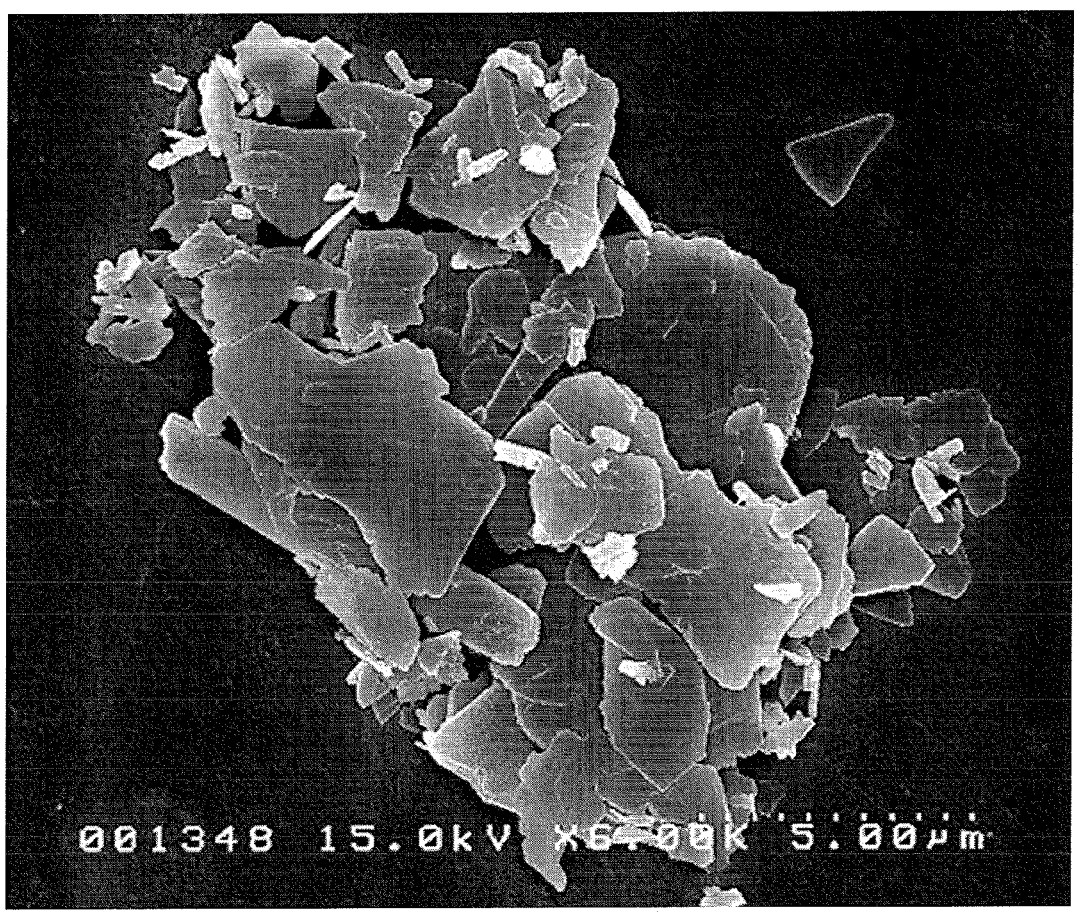
FIG. 4 is the microscope photograph that shows the detailed structure of the complex powder that is linked to embodiment 1 of this invention.

Zinc Oxide-Covering Talc (Covering as Spots): FIG. 4: Covering Quantity: 10% by Weight A 3 L separable reaction vessel was charged with 1000 mL of ion exchange water and 100 g of a talc (ζ-potential: −26.5 mV, average particle size: 16 μm), and fitted with a pH controller connected to two microtube pump and a stirrer. One microtube pump was connected to zinc chloride solution prepared by dissolving 16.75 g of zinc chloride and 2.4 ml of 5M aqueous solution of hydrochloric acid in 150 ml of ion exchange water and the other microtube pump was connected to alkaline solution prepared by dissolving 12 g of sodium hydroxide in 150 ml of ion exchange water, and the tubes were fixed to enable dropwise addition to the reaction vessel while controlling pH.

With stirring at room temperature, the reaction was conducted while adjusting the quantity of the two aqueous solution added dropwise so that pH was kept at 10. The time period of the dropwise addition was about 30 minutes. The resultant precipitation was washed with water and filtered 5 times repetitively, dried in an oven at 120° C. for 15 hours and then ground using a personal mill. The powder obtained was sieved through a 100 mesh sieve to obtain the intended material.

Embodiment 2

Figure 5:
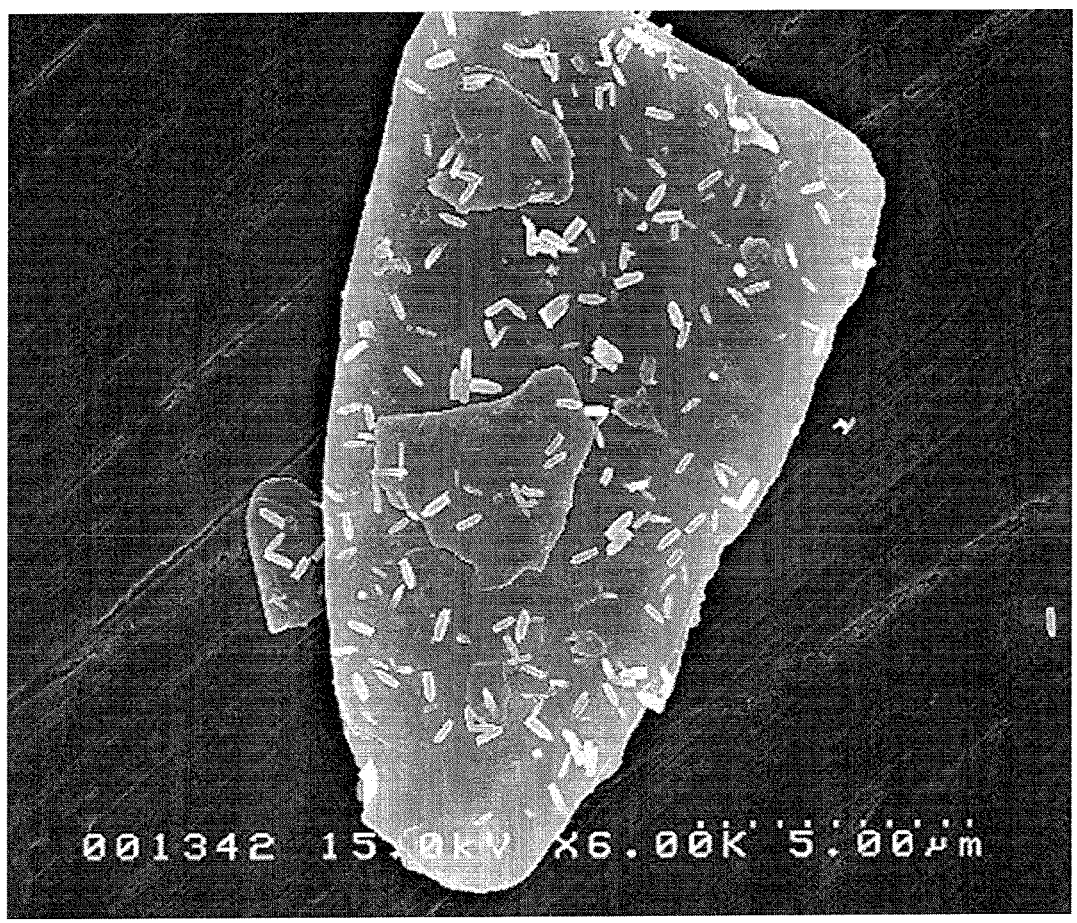
FIG. 5 is the microscope photograph that shows the detailed structure of the complex powder that is linked to embodiment 2 of this invention.

Zinc Oxide-covering Mica (Covering as Spots): FIG. 5: Covering Quantity: 10% by Weight The intended material was obtained similarly to Embodiment 1 except for using mica (ζ-potential: −36.1 mV, average particle size: 18 μm) instead of talc.

Embodiment 3

Figure 6:
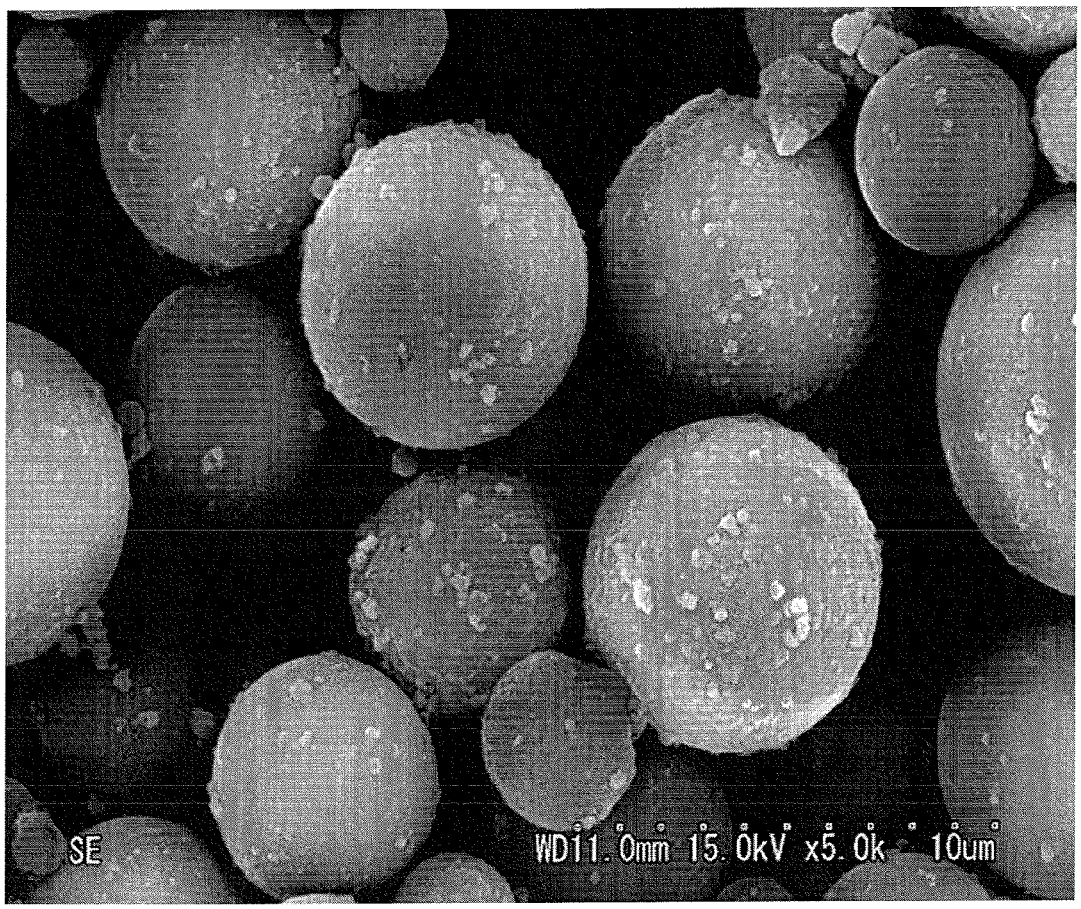
FIG. 6 is the microscope photograph that shows the detailed structure of the complex powder that is linked to embodiment 3 of this invention.

Zinc Oxide-covering Spherical Silica (Covering as Spots): FIG. 6: Covering Quantity: 10% by Weight The intended material was obtained similarly to Embodiment 1 except for using spherical silica (ζ-potential: −25.1 mV, average particle size: 5 μm) instead of talc.

Embodiment 4

Figure 7:
FIG. 7 is the microscope photograph that shows the detailed structure of the complex powder that is linked to embodiment 4 of this invention.

Zinc Oxide-covering Tabular Silica (Covering as Spots): FIG. 7: Covering quantity: 10% by weight The intended material was obtained similarly to Embodiment 1 except for using tabular silica (ζ-potential: −24.7 mV, average particle size: 4.5 μm) instead of talc.

Embodiment 5

Figure 8:
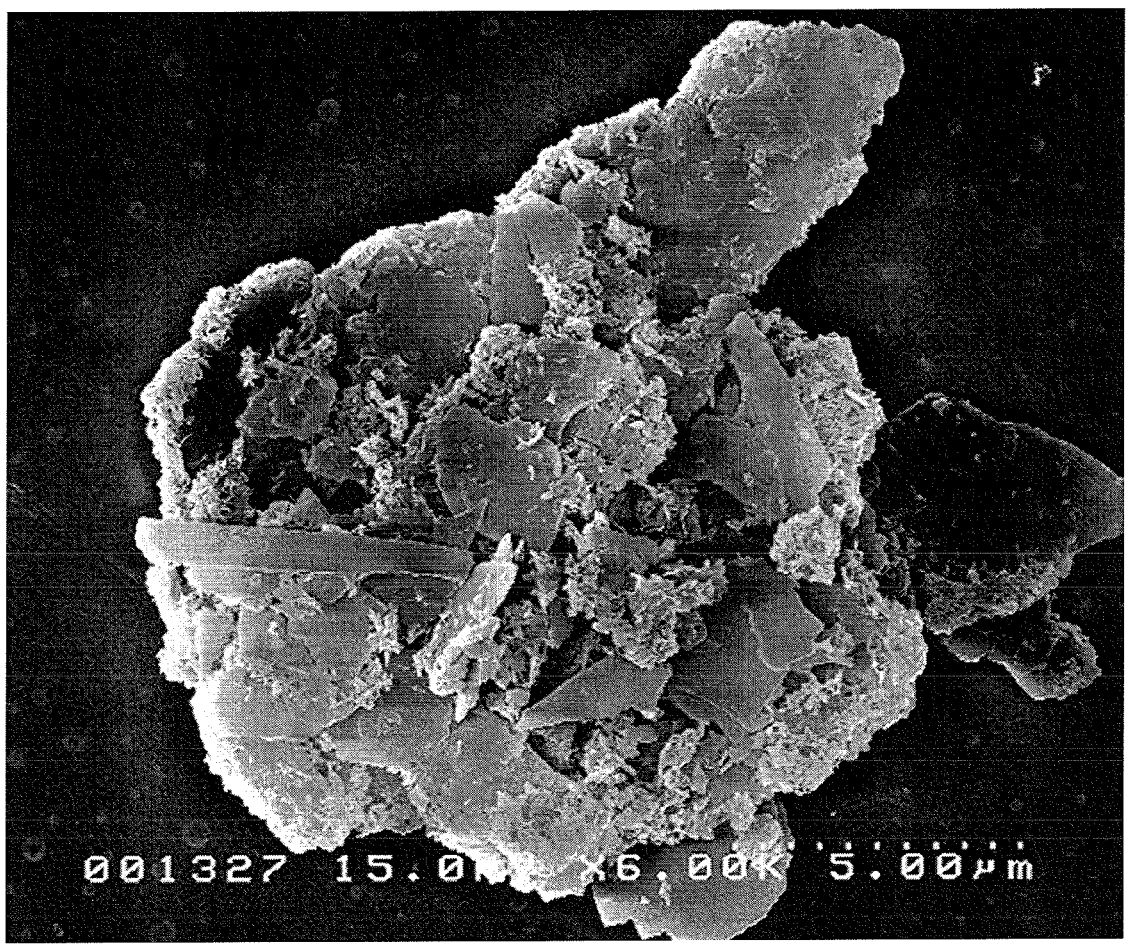
FIG. 8 is the microscope photograph that shows the detailed structure of the complex powder that is linked to embodiment 5 of this invention.

Zinc Oxide-covering Talc (Covering as Stripes): FIG. 8: Covering quantity: 10% by weight A 3 L separable reaction vessel was charged with 1000 mL of ion exchange water and 100 g of talc (ζ-potential: −26.5 mV, average particle size: 16 μm), and fitted with a pH controller connected to two microtube pump and a stirrer. One microtube pump was connected to zinc chloride solution prepared by dissolving 16.75 g of zinc chloride and 2.4 ml of 5M aqueous solution of hydrochloric acid in 150 ml of ion exchange water and the other microtube pump was connected to alkaline solution prepared by dissolving 6.52 g of sodium and 7.95 g of sodium hydroxide in 150 ml of ion exchange water, and the tubes were fixed to enable dropwise addition to the reaction vessel while controlling pH.

With stirring at room temperature, the reaction was conducted while adjusting the quantity of the two aqueous solution added dropwise so that pH was kept at 8. The time period of the dropwise addition was about 30 minutes. The resultant precipitation was washed with water and filtered 5 times repetitively, dried in an oven at 80° C. for 15 hours and then ground using a personal mill. The powder obtained was baked for 1 hour at 300° C. and sieved through a 100 mesh sieve to obtain the intended material.

Embodiment 6

Figure 9:
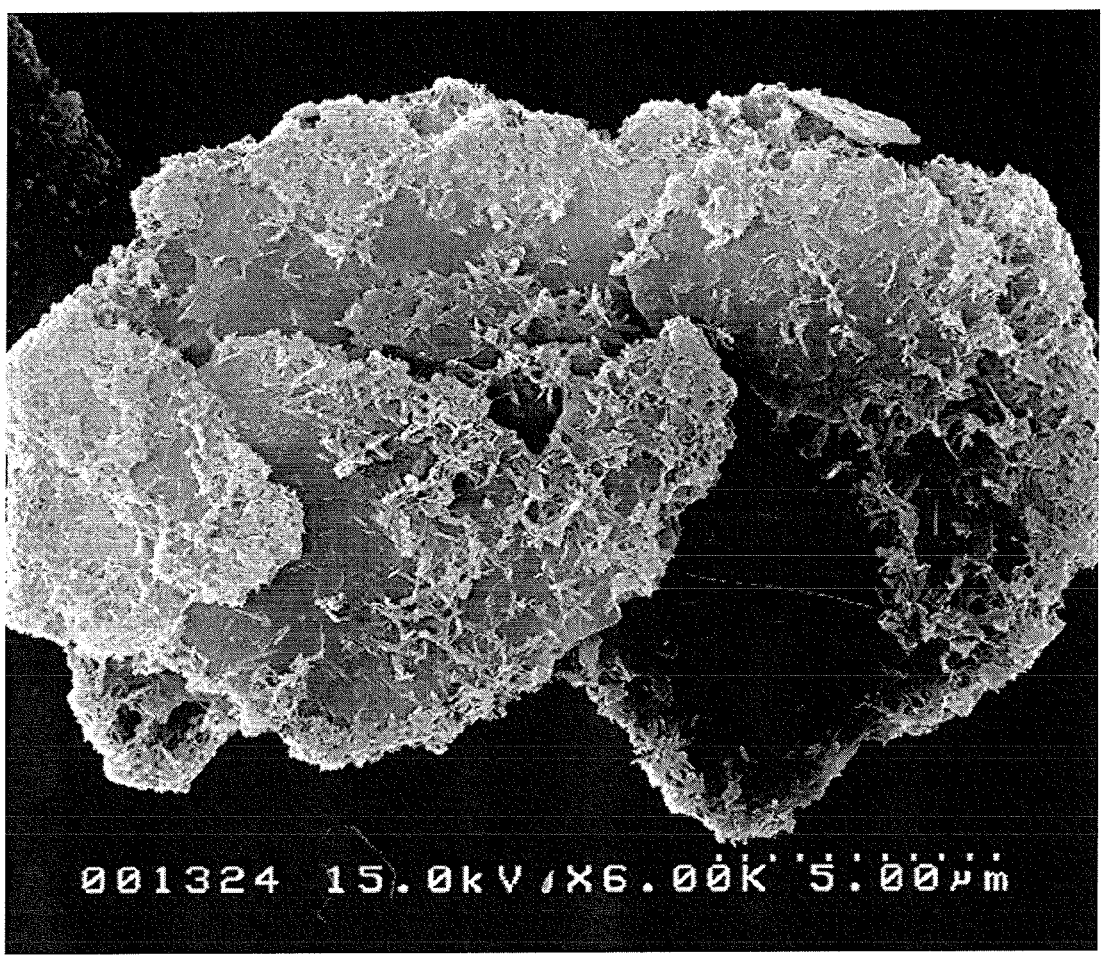
FIG. 9 is the microscope photograph that shows the detailed structure of the complex powder that is linked to embodiment 6 of this invention.

Zinc Oxide-covering Mica (Covering as Stripes):
FIG. 9: Covering quantity: 10% by weight The intended material was obtained similarly to Embodiment 5 except for using mica (ζ-potential: −36.1 mV, average particle size: 18 μm) instead of talc.

Embodiment 7

Figure 10:
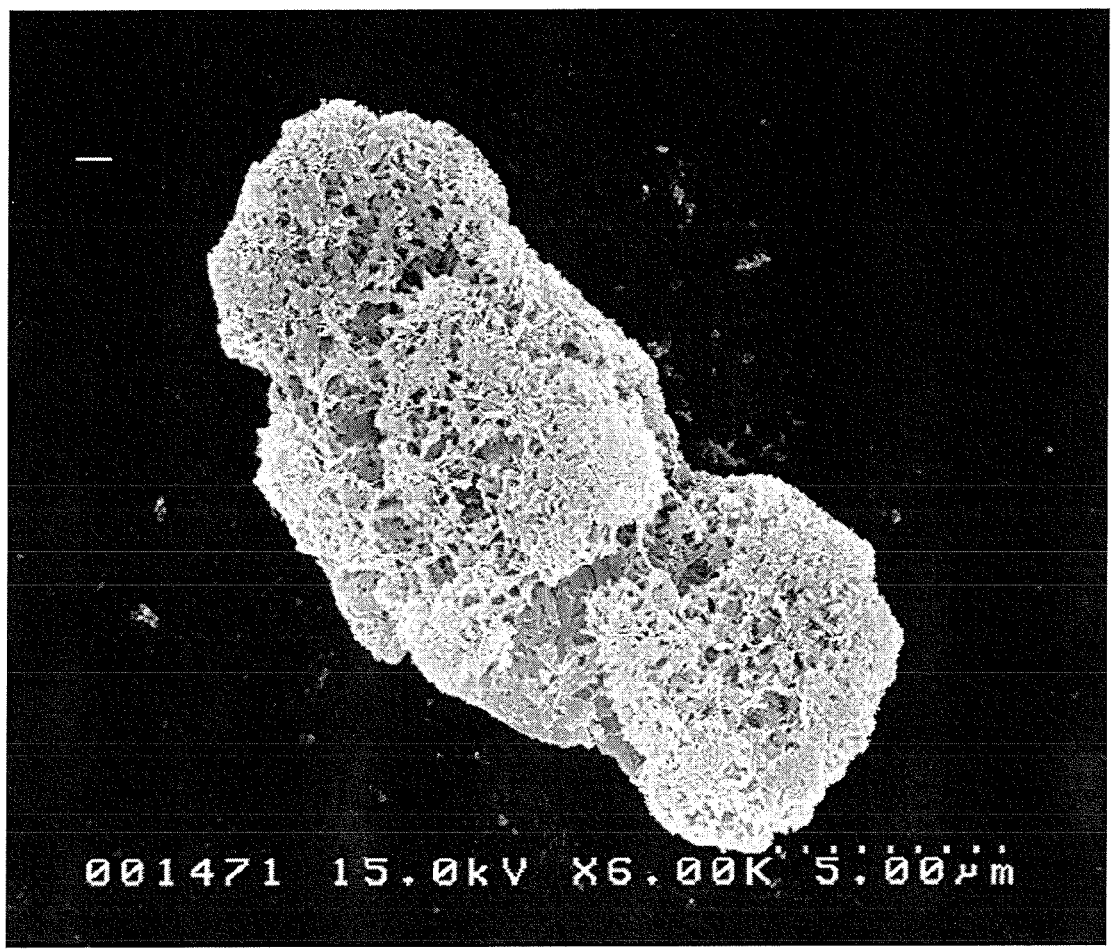
FIG. 10 is the microscope photograph that shows the detailed structure of the complex powder that is linked to embodiment 7 of this invention.

Zinc Oxide-covering Silica (Covering as Stripes):
FIG. 10: Covering quantity: 50% by weight The intended material was obtained similarly to Embodiment 5 except for elevating covering quantity of zinc oxide from 10% to 50% by increasing the amount of each mixture solution added dropwise.

Comparative 1 Talc on the market
Comparative 2 Mica on the market
Comparative 3 Silica on the market
Comparative 4 Zinc oxide (spot state synthesis method)

A 1 L separable reaction vessel was charged with 300 mL of ion exchange water, and fitted with a pH controller connected to two microtube pump and a stirrer. One microtube pump was connected to zinc chloride solution prepared by dissolving 16.75 g of zinc chloride and 2.4 ml of a 5M aqueous solution of hydrochloric acid in 150 ml of ion exchange water and the other microtube pump was connected to an alkaline solution prepared by dissolving 12 g of sodium hydroxide in 150 ml of ion exchange water, and the tubes were fixed to enable dropwise addition to the reaction vessel while controlling pH.

With stirring at room temperature, the reaction was conducted while adjusting the quantity of the two aqueous solution added dropwise so that pH was kept at 10. The time period of the dropwise addition was about 30 minutes. The resultant precipitation was washed with water and filtered 5 times repetitively, dried in an oven at 120° C. for 15 hours and then ground using a personal mill. The powder obtained was sieved through a 100 mesh sieve to obtain the intended material.

TABLE 5

| Sample | Adsorption site | Form of adsorption site | Operation site | Form of operation site |
|---|---|---|---|---|
| Embodiment 1 | Talk | Tabular | Zinc oxide | Covering as spots |
| Embodiment 2 | Mica | Tabular | Zinc oxide | Covering as spots |
| Embodiment 3 | Silica | Spherical | Zinc oxide | Covering as spots |
| Embodiment 4 | Silica | Tabular | Zinc oxide | Covering as spots |
| Embodiment 5 | Talk | Tabular | Zinc oxide | Covering as stripes |
| Embodiment 6 | Mica | Tabular | Zinc oxide | Covering as stripes |
| Embodiment 7 | Silica | No Fixed form | Zinc oxide | Covering as stripes |
| Comparative 1 | Talk | Tabular | — | — |
| Comparative 2 | Mica | Tabular | — | — |
| Comparative 3 | Silica | No Fixed form | — | — |
| Comparative 4 | — | — | Zinc oxide | Covering as spots |

| Covering quantity (% by weight) | ζ-potential (mV) | Adsorption rate (%) | Inhibition rate (%) | Prevention effect |
|---|---|---|---|---|
| Embodiment 1 | | | | |
| 10 | −1.4 | 65 | 60 | AA |
| Embodiment 2 | | | | |
| 10 | −1.2 | 58 | 50 | AA |
| Embodiment 3 | | | | |
| 10 | −20.6 | 64 | 50 | AA |
| Embodiment 4 | | | | |
| 10 | −9.3 | 60 | 51 | AA |
| Embodiment 5 | | | | |
| 10 | +4.0 | 52 | 49 | A |
| Embodiment 6 | | | | |
| 10 | +3.6 | 56 | 47 | A |
| Embodiment 7 | | | | |
| 50 | +5.0 | 50 | 43 | A |
| Comparative 1 | | | | |
| — | −26.5 | 68 | 15 | C |
| Comparative 2 | | | | |
| — | −36.1 | 68 | 10 | C |
| Comparative 3 | | | | |
| — | −25.1 | 82 | 5 | C |
| Comparative 4 | | | | |
| — | +11.7 | 45 | 38 | B |

As evident from Table 5, the effect of a rough skin was almost proportionated to inhibition rate of the plasminogen activator. One with a inhibition rate of 40% or higher had a high rough skin-preventing effect, and one with a inhibition rate of 50% or higher had a marked effect.

Any of complex powders of this invention exhibited relatively high adsorption rate and inhibition rate, and had a high effect on the rough skin, While the talc, silica and mica exhibited excellent UK adsorption rates since their ζ-potentials were not higher than −10 mV, any of them exhibited almost no UK inhibiting effect when employed alone and showed no rough skin-preventing effect (Comparatives 1 to 3).

The rough skin-preventing effect was more excellent at zinc oxide-covering quantity of 50% by weight (Embodiment 7) than zinc oxide-covering quantity of 10% by weight (Embodiment 1). This may be attributable to the tendency of a reduction in the UK activity inhibiting effect due to the difficulty in adsorbing the UK resulting from the coverage of absorption sites of talc due to an excessive amount of covering of zinc oxide.

While ζ-potential of the overall complex powder in each of Embodiments 5 to 7 was positive, a rough skin-protecting effect was exhibited. Since ζ-potential at the adsorption site where is not covered with the zinc oxide was negative, UK could still be adsorbed.

Zinc Oxide Covering Quantity and UK Activity Inhibition Rate

The relationship between zinc oxide covering quantity and UK activity inhibition rate was investigated using a zinc oxide-covering talc.

Figure 11:
FIGS. 11A-11D are photomicrographs detailing the structure of talc covered with zinc oxide at weight percent rates of 0%, 5%, 10%, and 30%, respectively, all according to Embodiment 1.
Figure 11:
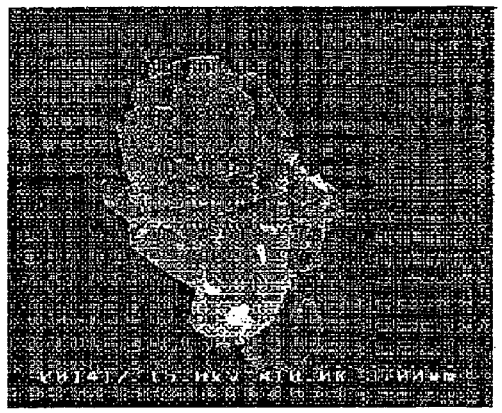
Figure 11:
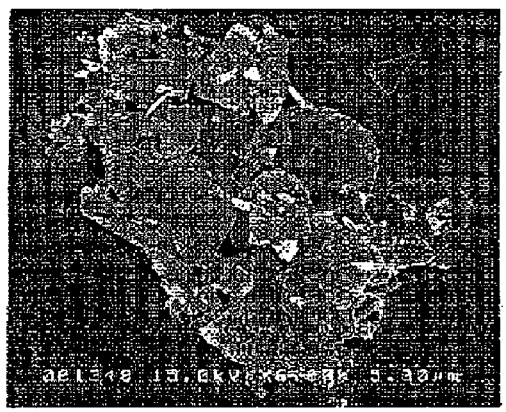
Figure 11:
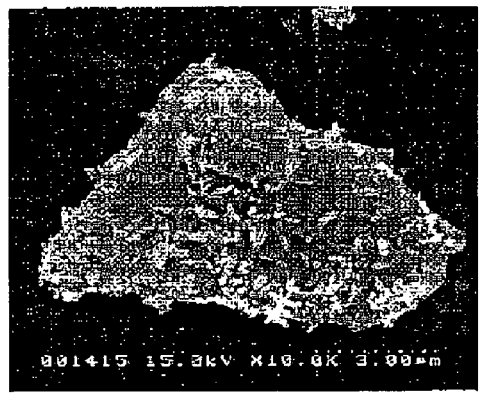

Similarly to Embodiment 1, zinc oxide-covering talcs having various zinc oxide-covering quantity were obtained (FIG. 11).

TABLE 6

| ZnO covering quantity (% by weight) | UK active inhibition rate (%) | ζ-potential (mV) | |
|---|---|---|---|
| 0 | 26 | −19.3 | (FIG. 11 A) |
| 5 | 53 | −7.5 | (FIG. 11 B) |
| 10 | 58 | −2.1 | (FIG. 11 C) |
| 30 | 56 | +9.1 | (FIG. 11 D) |

In zinc oxide-covering talc, UK is adsorbed onto the surface of the talc, and zinc ion inhibits UK activity.

At covering quantity up to 10% by weight, increased covering quantity of zinc oxide resulted in increased UK inhibition rate, while at 30% covering quantity the UK inhibition rate was rather reduced.

These findings may be attributable to the difficulty in allowing zinc ion to inhibit UK activity due to the difficulty in adsorbing UK as a result of too high ζ-potential because of an excessive amount of the covering of the zinc oxide. As a result of a further investigation, it was revealed that the UK inhibiting effect (UK inhibition rate: 40% or higher) was obtained with a covering rate of 1 to 70% weight.

Accordingly, it is preferable that in a complex powder having an operation site formed on an adsorption site the covering quantity of the operation site is 1 to 70% by weight.

Zinc Oxide Covering Rate and UK Activity Inhibition Rate

The relationship between zinc oxide covering rate (surface area) and the UK activity inhibition rate was investigated.

Figure 12:
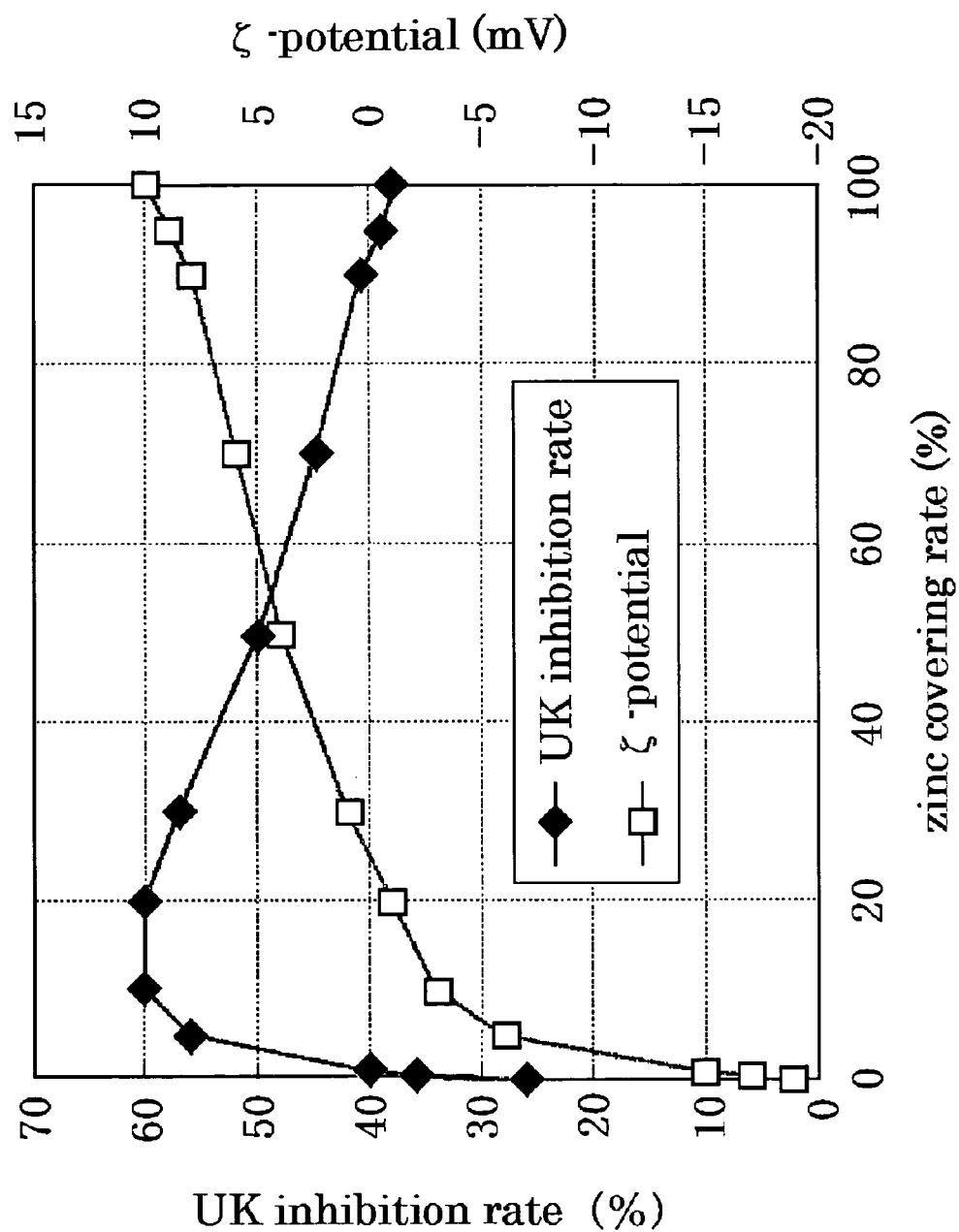
FIG. 12 shows the relation between the zinc oxide covering rate and UK inhibition rate, and ζ-potential in talc covered with zinc oxide according to Embodiment 1.

Similarly to Embodiment 1, zinc oxide-covering talcs having various coverings rate of zinc oxide were obtained. The results are shown in Table 7 and FIG. 12.

TABLE 7

| Zinc oxide covering rate (%) | UK active inhibition rate (%) | ζ-potential (mV) |
|---|---|---|
| 0 | 26 | −19 |
| 0.5 | 36 | −17 |
| 1 | 40 | −15 |
| 5 | 56 | −6 |
| 10 | 60 | −3 |

TABLE 7-continued

| Zinc oxide covering rate (%) | UK active inhibition rate (%) | ζ-potential (mV) |
|---|---|---|
| 20 | 60 | −1 |
| 30 | 57 | +1 |
| 50 | 50 | +4 |
| 70 | 45 | +6 |
| 90 | 41 | +8 |
| 95 | 39 | +9 |
| 100 | 38 | +10 |

At covering rate up to 20% by weight, an increased zinc oxide covering rate resulted in increased UK inhibition rate, but once exceeding 20% covering an increased zinc oxide covering rate rather resulted in reduced UK inhibition rate. These findings may be due to the difficulty in allowing the zinc ion to inhibit the UK activity resulting from the coverage of the silica's absorption sites due to an excessive amount of the covering of the zinc oxide and also resulting from reduced UK absorption ability due to elevated ζ-potential because of the covering of the zinc oxide. As evident from FIG. 12, inhibition rate of 40% or higher is obtained at covering rate of 1 to 90%, inhibition rate of 45% or higher is covering rate of 2 to 70%, and inhibition rate of 50% or higher is covering rate of 4 to 50%.

Accordingly, it is preferable that in a complex powder having an operation site formed on the surface of an adsorption site, the covering rate of the operation site is 1 to 90% by weight, typically 2 to 70%, especially 4 to 50%.

While the ζ-potential of the overall complex powder was positive at zinc oxide covering rate of 25% or higher, the UK could still be adsorbed since the ζ-potential at the adsorption site not covered with the zinc oxide was negative, whereby exhibiting UK activity inhibiting effect.

ζ-Potential and Zinc Ion Elution Level

In zinc oxide-covering organic powder, UK is adsorbed onto the surface of the organic powder and the zinc ion inhibits UK activity.

The level of zinc ion eluted from various zinc oxide-covering organic powders was measured, and the relationship with UK activity inhibition rate was investigated.

Zinc Oxide/Organic Powder Complex Formation

Organic powders and zinc oxide (Zinc white SEIDO) were mixed preliminary, and said organic powders were covered with said zinc oxide by a mechanofusion processing, whereby producing complex powders shown in Table 8. The mechanofusion processing is a procedure in which mixed powders are agitated at a high rotation speed and the powders hit against each other during the passage through narrow gaps whereby forming a complex powder.

Organic Powders

Polyamide (Nylon SP500™: ζ-potential: −32 mV)

Polymethyl methacrylate (Ganzpearl™: ζ-potential: −18 mV)

Silicone resin microparticle (Tospearl 145A™: ζ-potential: −14 mV)

Figure 13:
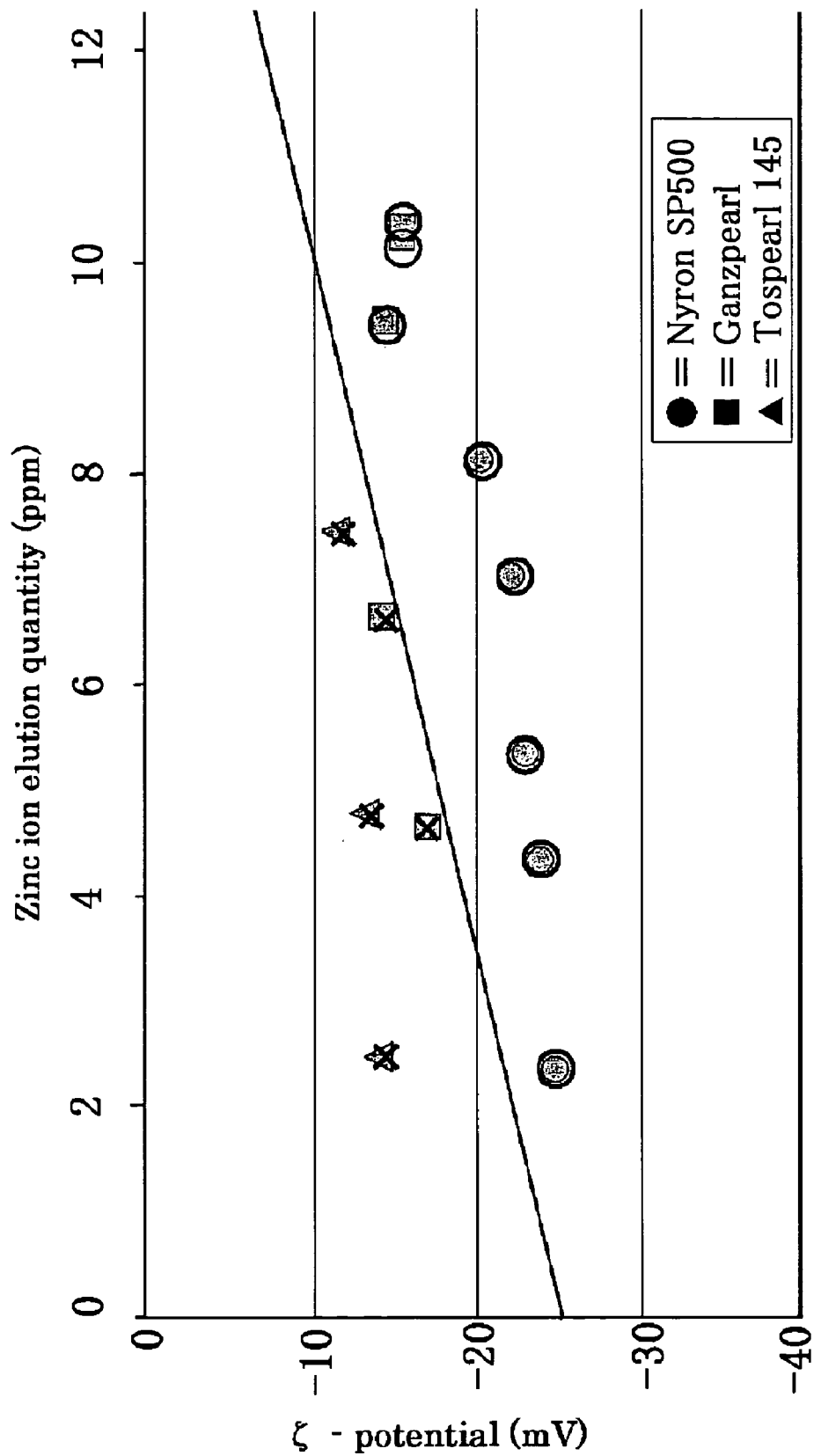
FIG. 13 shows the relation between ζ-potential and zinc ion elution quantity of organic powder covered in zinc oxide prepared by a mechanofusion process, producing the complex powders of Table 8. The O indicates a UK inhibition rate of 40% or higher, and the X indicates a rate of less than 40%.

The relationship between zinc ion elution level and UK inhibition rate is shown in FIG. 13 with designating ○ when UK inhibition rate is 40% or higher, and x when less than 40%.

TABLE 8

| | Covering quantity of zinc oxide (% by weight) | ζ-potential (mV) | Zinc ion concentration (ppm) | UK inhibition rate (%) |
|---|---|---|---|---|
| Polyamide (Nylon SP500 ™) | 10 | −25 | 2.3 | 50 |
| | 20 | −24 | 4.3 | 50 |
| | 30 | −23 | 5.4 | 59 |
| | 40 | −22 | 7.1 | 51 |
| | 50 | −20 | 8.1 | 49 |
| Polymethyl methacrylate (Ganzpearl ™) | 10 | −17 | 4.7 | 31 |
| | 20 | −14 | 6.8 | 34 |
| | 30 | −14 | 9.5 | 47 |
| | 40 | −15 | 10.2 | 47 |
| | 50 | −15 | 10.3 | 46 |
| Silicone resin microparticle (Tospearl 145A ™) | 10 | −14 | 2.5 | 36 |
| | 20 | −13 | 4.8 | 35 |
| | 40 | −11 | 7.5 | 36 |

As evident from FIG. 13, it was confirmed that UK inhibition effect is demonstrated, when ζ-potential is below the slanting line in FIG. 13. Accordingly, it is preferable that ζ-potential≦zinc ion elution level×1.5-25.

It was also revealed that the complex powder of the Nylon SP 500™ and the zinc oxide exhibited a rough skin-preventing effect.

Figure 14:
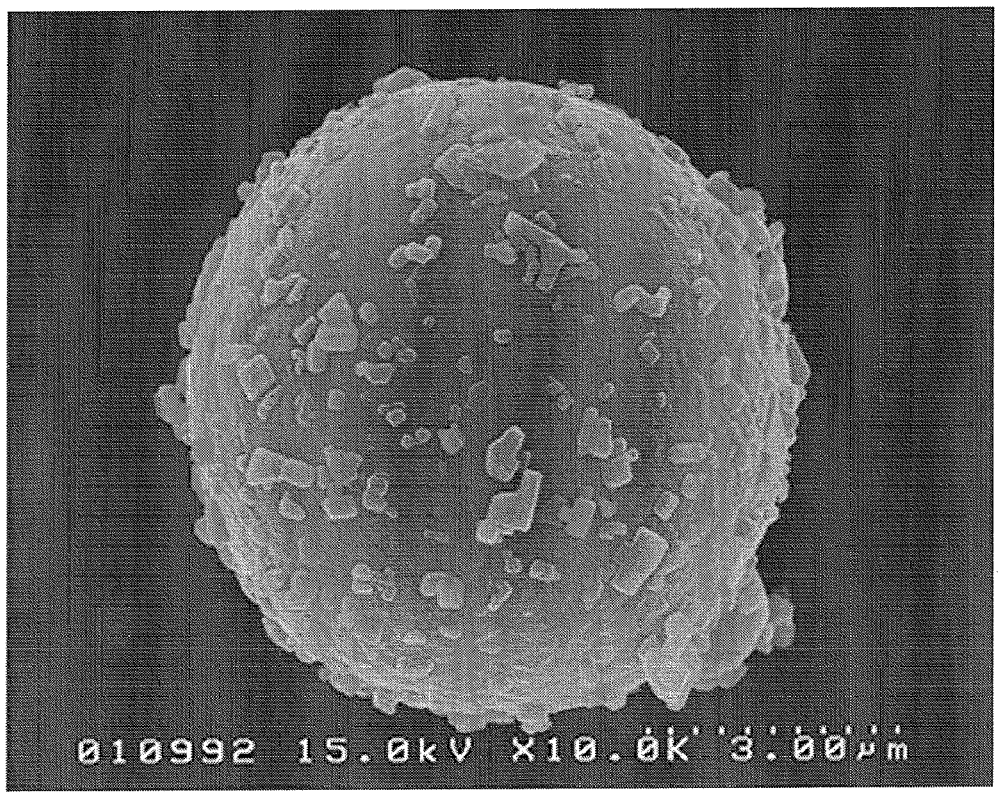
FIG. 14 is the microscope photograph that shows the detailed structure of zinc oxide-covering polyamide that is the complex powder of this invention.
Figure 14:
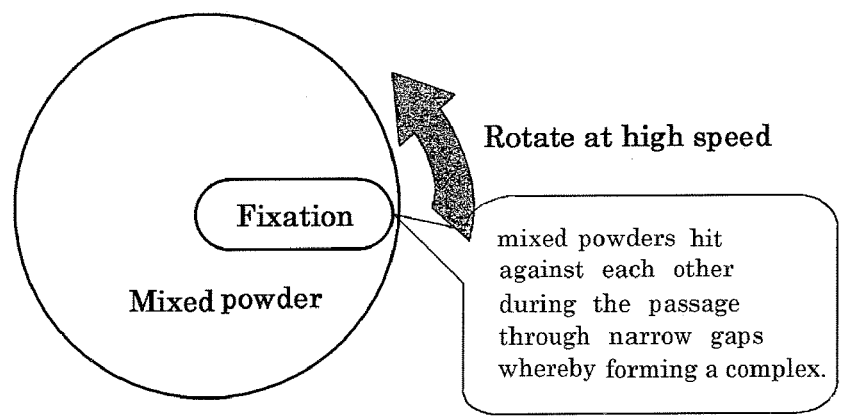

The microscopic photograph of the polyamide covered with 30% by weight of the zinc oxide is shown in FIG. 14.

Embodiment 8

A powder of talc covered with each of amino acids shown below was further covered (by the mechanofusion treatment) with zinc oxide (Zinc white manufactured by SEIDO) to produce a complex powder (covering at 30% by weight). Any of the powders had UK activity inhibition rate of about 40% and proven to have a sufficient inhibiting effect.

$N^e$-lauroyl-L-lysine (amphoteric)

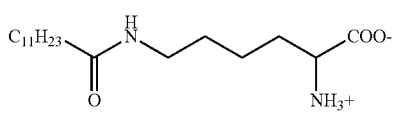

di-Sodium N-stearoyl-L-glutamate (anion)

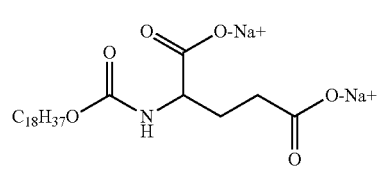

Poly sodium aspartate (anion)

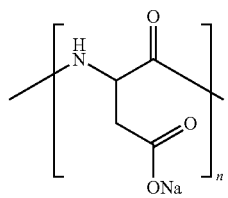

(B) Complex Powder Having Adsorption Site Formed on Operation Site (Silica-covering Zinc Oxide)

Embodiment 9

1.2% Silica-Covering Zinc Oxide (Covering as Network)

20 Kg of a zinc oxide powder is filled in a reaction device, which is then subjected to a reduced pressure and purged with nitrogen, and then the internal temperature is raised to 60° C. 1,3,5,7-Tetramethylcyclotetrasiloxane is fed at a rate of 40 to 50 g/hr into the device, where it is reacted with the surface of the zinc oxide. Once the silicon deposition rate reached an optimum value of 0.5% to 10%, the internal temperature is raised to 105° C. to sinter for 2 hours. After replacing with nitrogen, the system is allowed to stand to cool to room temperature. The sample thus synthesized is taken out, ground and disintegrated, sieved through a 100 mesh sieve, sintered for several hours at an optimum temperature of 400 to 700° C. at which the silicone is converted into a silica using an electric furnace, disintegrated, whereby obtaining the intended material.

Embodiment 10

1.6% Silica-Covering Zinc Oxide (Covering as Network)

20 kg of a zinc oxide powder is filled in a Henschel mixer, to which 200 to 600 g of methyl hydrogen polysiloxane (Shin-Etsu Chemical Co., Ltd.) or a silane coupling agent (octyl trimethoxysilane, octyl triethoxysilane, methyl trimethoxysilane, methyl triethoxysilane, dimethyl diethoxysilane, hexamethyl disilazane: Shin-Etsu Chemical Co., Ltd.) dissolved in 400 g of hexane is added with stirring. A powder in which the silicone is dispersed uniformly is subjected to the reaction of the silicone with the surface of the powder at 150° C. whereby evaporating the solvent. The powder is taken out, sintered for several hours at an optimum temperature of 400 to 700° C. at which the silicone is converted into a silica using an electric furnace, disintegrated, whereby obtaining the intended material.

Comparative 5

Silica-Covering Zinc Oxide on the Market (Covering Entire Surface of Zinc Oxide)

TABLE 9

| Sample | Operation site | Adsorption site | Form of adsorption site |
|---|---|---|---|
| Embodiment 9 | Zinc oxide | Silica | Covering as network |
| Embodiment 10 | Zinc oxide | Silica | Covering as network |
| Comparative 5 | Zinc oxide | Silica | Covering entire surface |

| Sample | Covering rate (%) | ζ-potential (mV) | Inhibition rate (%) | Prevention effect |
|---|---|---|---|---|
| Embodiment 9 | 1.2 | −12.6 | 52 | AA |
| Embodiment 10 | 1.6 | −13.2 | 53 | AA |
| Comparative 5 | 100 | −18.5 | 37 | B |

As evident from Table 9, silica-covering entire surface of zinc oxide (Comparative 5) showed the effect which was lower than that of silica network-covering zinc oxide (Embodiments 9 and 10). This may be due to the disability of inhibiting UK activity when the entire surface of zinc oxide was covered with silica.

Silica Covering Quantity and UK Activity Inhibition Rate Zinc Ion Elution Level

Then a silica-covering zinc oxide was employed to investigate the relationship between the silica covering quantity and UK activity inhibition rate or zinc ion elution level.

Similarly to Embodiment 9, silica-covering zinc oxides with various silica covering quantities were obtained.

The results are shown in Table 10 and FIG. 15.

TABLE 10

| Silica covering quantity (% by weight) | UK active inhibition rate (%) | ζ-potential (mV) | Zinc ion elution quantity (ppm) |
|---|---|---|---|
| 0 | 36 | 5.2 | 42.5 |
| 0.5 | 44 | −0.2 | 38.5 |
| 1 | 49 | −3.8 | 35.2 |
| 10 | 54 | −10.0 | 17.6 |
| 20 | 57 | −11.3 | 8.9 |
| 30 | 56 | −12.6 | 4.4 |
| 50 | 50 | −12.8 | 1.2 |
| 70 | 42 | −12.7 | 0.87 |
| 80 | 39 | −13.0 | 0.45 |

In silica-covering zinc oxide, zinc ion and UK are adsorbed onto the surface silica, and zinc ion inhibits UK activity.

At covering quantity up to 20% by weight, an increased silica covering quantity resulted in increased UK inhibition rate, but once exceeding 20% covering quantity increased silica covering quantity rather resulted in reduced UK inhibition rate. These findings may be due to the difficulty in allowing zinc ion to be eluted at an excessive silica covering quantity, which leads to the difficulty in exerting UK activity inhibition. As evident from FIG. 15, it was revealed that inhibition rate of 40% or higher required a covering rate of 0.1 to 75% by weight, and inhibition rate of 50% or higher required a covering rate of 3 to 50% by weight.

Accordingly, it is preferable that in complex powder of this invention having an adsorption site formed on the surface of an operation site, covering rate of the absorption site is preferably 0.1 to 75% by weight, especially 3 to 50% by weight.

Also as evident from FIG. 15, zinc ion elution level was 0.7 to 40 ppm at 40% inhibition or higher, and zinc ion elution level was 1.2 to 30 ppm at 50% inhibition or higher. While the presence of the zinc ion at a high concentration may not be preferable in view of the preparation of a pharmaceutical such as an external composition, the complex powder of this invention is preferred since it exhibits UK inhibiting effect even at low concentration of the zinc ion.

Embodiment 11

A zinc oxide was covered with each of anionic polymers shown in Table 11 to form complex powder, whose UK inhibition rate was investigated. The results are shown in Table 12.

Method for Producing Anionic Polymer-covering Zinc Oxide

Each of various anionic polymers is dissolved in a good solvent, to which a zinc oxide is added. After mixing sufficiently, the sample is filtered and washed, and dried sufficiently.

TABLE 11

| Kinds of polymers | Solubility to water |
|---|---|
| Acrylate/t-Octyl propene amide copolymer | Difficult to dissolve |
| Carboxy vinyl polymer | Soluble |
| Polystyrene sulfonate | Soluble |
| Polyacrylamide methyl propane sulfonate | Soluble |

TABLE 12

| Kinds of polymers | Covering quantity (% by weight) | ζ-potential (mV) | Zinc ion concentration (ppm) | Inhibition rate(%) |
|---|---|---|---|---|
| Acrylate/t-Octyl propene amide copolymer | 0.5 | −13 | 7.9 | 55 |
| Carboxy vinyl polymer | 1.1 | −20 | 6.4 | 40 |
| Polystyrene sulfonate | 0.4 | −27 | 27.9 | 40 |
| Polystyrene sulfonate | 0.6 | −29 | 27.2 | 56 |
| Polyacrylamide methyl propane sulfonate | 0.5 | −20 | 22.9 | 43 |

It was confirmed that all complex powders above have sufficient inhibition ability.

A complex powder according to the present invention exhibits not only a promotive effect on a rough skin-improving effect but also a irritation-reducing effect on a sensitive skin having a pathological dermal inflammations.

On the other hand, a complex powder having a marked effect was imparted with a water-repelling ability by the treatment with 3% silicone to obtain a sample, which was, however, not dispersed in the assay system because of its hydrophobicity and was not able to be examined for the inhibition rate (N.D.), but it still exhibited a sufficient rough skin-preventing effect when used actually, although the effect was lower than that of a non-treated complex powder.

The effect of a complex powder of the present invention was examined for the rough skin-improving effect and the skin irritating effect on the skin condition of a sensitive skin. As samples, a powdery foundation blended with 10% by weight of the zinc oxide-covering talc (Embodiment 12) and a non-blended powdery foundation (Comparative 7) having the compositions (% by weight) shown in Table 13 were employed.

The Embodiment 12 was applied to one cheek of each of the 50 female panelists having the sensitive skins described above once a day or more for 8 weeks while applying the Comparative 7 to the other cheek, and the subsequent skin condition was evaluated on the basis of the following criteria.

[1] Criterion of Skin Condition-improving Effect
Very good: The skin condition became markedly improved.
Good: The skin condition became improved.
Slightly good: The skin condition became slightly improved.
Poor: The skin condition was unchanged or rather exacerbated.
<Evaluation of Improving Effect on Skin Condition>
AA: The efficacy rate (The ratio of the panelists answering "Very good", "Good" and "Slightly good") is 80% or higher.
A: The efficacy rate is 50% or higher and less than 80%.
B: The efficacy rate is 30% or higher and less than 50%.
C: The efficacy rate is less than 30%.
[2] Skin Irritating Feel
<Evaluation of Skin Irritating Feel>
AA: The ratio of the panelists experiencing irritating feel on the skin is 0%.
A: The ratio of the panelists experiencing irritating feel on the skin is less than 5%.
B: The ratio of the panelists experiencing irritating feel on the skin is 5% or more and less than 10%.
C: The ratio of the panelists experiencing a stingy feel on the skin is 10% or more.
[3] Criterion by Replica Method
Simultaneously with the visual examination of the skin condition, a skin replica was obtained by subjecting the skin surface morphology to a replica method using a myricin resin, and observed microscopically (×17) and evaluated.
<Replica Method Evaluation>
1: Skin groove and skin convex were lost and horny layer was peeled over a wide area.
2: Skin groove and skin convex were unclear and horny layer was peeled.
3: Skin groove and skin convex were observed but rather flat.
4: Skin groove and skin convex were clear.
5: Skin groove and skin convex were clear and well-regulated.

TABLE 13

|  |  | Embodiment 12 | Comparative 7 |
|---|---|---|---|
| Zinc oxide covering talc |  | 10.0 | — |
| Mica |  | 36.0 | 36.0 |
| Talc |  | Remainder | Remainder |
| Spherical PMMA powder |  | 8.0 | 8.0 |
| Spherical silica powder |  | 3.0 | 3.0 |
| Titanium oxide |  | 7.5 | 7.5 |
| Red iron oxide |  | 2.0 | 2.0 |
| Yellow iron oxide |  | 3.0 | 3.0 |
| Black iron oxide |  | 0.2 | 0.2 |
| Ester oil |  | 2.0 | 2.0 |
| Silicone oil |  | 4.0 | 4.0 |
| Hydrocarbon oil |  | 2.0 | 2.0 |
| Sorbitan sesquiisostearate |  | 1.0 | 1.0 |
| Antioxidant |  | Proper quantity | Proper quantity |
| [1] Skin condition-improving effect |  | A | C |
| [2] Skin irritating feel |  | AA | A |
| [3] Replica evaluation | 1 | none | 4 people |
|  | 2 | 4 people | 9 people |
|  | 3 | 8 people | 17 people |
|  | 4 | 29 people | 18 people |
|  | 5 | 9 people | 2 people |
|  | Total | 50 people | 50 people |

As evidence from Table 13, the sample of Embodiment 12 supplemented with oxide-covering talc of the present invention exhibited a more excellent improving effect on the sensitive skin than the sample of the Comparative 7, without exhibiting any skin irritating effect.

Preferred formulations of the present invention are shown below. Any of these formulations exhibited excellent preventing ability and improving ability against a rough skin as well as improving effect on an atopic dermatitis, pimples and the like while showing an extremely low irritation to a sensitive skin or allergic skin.

| Blending example 1 Cream | |
|---|---|
| (Prescription) | % by weight |
| 1) Monoglycerol stearate | 2.0 |
| 2) Stearyl alcohol | 4.0 |
| 3) Bee wax | 3.0 |
| 4) Lanolin | 5.0 |
| 5) Ethylparaben | 0.3 |
| 6) P.O.E (20) sorbitan monooleate | 2.0 |
| 7) Squalane | 20.0 |
| 8) Zinc oxide-covering talc | 5.0 |
| 9) Perfume | 0.2 |
| 10) 1,3-Butylene glycol | 5.0 |
| 11) Glycerin | 5.0 |
| 12) Purified water | remainder |

(The Process)
The Components 1) to 7) and 9) are heated and kept at 75° C. (oil phase). The Components 10) and 11) are dissolved in the Component 12), to which then the Component 8) is added, dispersed and warmed at 75° C. (water phase). The water phase is added to the oil phase, emulsified uniformly using a homomixer, and cooled to 30° C. with stirring thoroughly.

| Blending example 2 Powder state external preparation | |
|---|---|
| (Prescription) | % by weight |
| 1) Talc | 49.95 |
| 2) Zinc oxide-covering silica | 50.0 |
| 3) Perfume | 0.05 |

(The Process)
The Components 1) and 2) are stirred and mixed thoroughly using a blender while spraying the Component 3) uniformly.

| Blending example 3 Baby powder | |
|---|---|
| (Prescription) | % by weight |
| 1) Talc | 77.0 |
| 2) Calcium carbonate | 17.0 |
| 3) Starch | 0.5 |
| 4) Zinc oxide-covering silica | 5.0 |
| 5) Germicide | 0.3 |
| 6) Antiseptics | 0.2 |

(The Process)
The Components 1) to 6) are stirred and mixed thoroughly using a blender

| Blending example 4 Lipstick | |
|---|---|
| (Prescription) | % by weight |
| 1) Hydrocarbon wax | 3.0 |
| 2) Candelilla wax | 1.0 |
| 3) Glyceryl isostearate | 41.0 |

-continued

| Blending example 4 Lipstick | |
|---|---|
| (Prescription) | % by weight |
| 4) Liquid paraffin | 46.448 |
| 5) Red number 202 | 0.5 |
| 6) Red number 204 | 2.0 |
| 7) Red number 223 | 0.05 |
| 8) Zinc oxide-covering mica | 2.0 |
| 9) Titanium dioxide | 4.0 |
| 10) Perfume | 0.002 |

(The Process)

The Components 1) to 4) are heated and dissolved at 85° C., combined with the Components 5) to 9), stirred and mixed and then combined with the Component 10) with stirring, charged into a container and cooled.

| Blending example 5 Emulsion-type foundation | |
|---|---|
| (Prescription) | % by weight |
| 1) Stearic acid | 0.4 |
| 2) Isostearic acid | 0.3 |
| 3) Cetyl 2-ethylhexanoate | 4.0 |
| 4) Liquid paraffin | 11.0 |
| 5) P.O.E (10) stearyl ether | 2.0 |
| 6) Talc | 15.0 |
| 7) Red iron oxide | 0.01 |
| 8) Yellow iron oxide | 0.001 |
| 9) Black iron oxide | 0.05 |
| 10) Cetyl alcohol | 0.3 |
| 11) Antiseptics | 0.07 |
| 12) Zinc oxide-covering silica | 5.0 |
| 13) Triethanolamine | 0.4 |
| 14) Propylene glycol | 5.0 |
| 15) Perfume | 0.01 |
| 16) Purified water | remainder |

(The Process)

The Components 1) to 11) are heated and dissolved/dispersed at 85° C., and then combined with the Component 12), which is dispersed uniformly. To this mixture, the Components 13), 14) and 16) which was dissolved and mixed with heating at 85° C. is added in portions to give an emulsion. The emulsifying temperature is kept for 10 minutes with stirring, the mixture is cooled to 45° C. with stirring. To this mixture, the Component 15) was added, cooled to 35° C. with stirring, and then charged into a container.

| Blending example 6 Pack | |
|---|---|
| (Prescription) | % by weight |
| 1) Polyvinyl alcohol | 15.0 |
| 2) Polyethylene glycol | 3.0 |
| 3) Propylene glycol | 7.0 |
| 4) Ethanol | 10.0 |
| 5) Zinc oxide-covering silica | 10.0 |
| 6) Methylparaben | 0.05 |
| 7) Perfume | 0.1 |
| 8) Purified water | remainder |

(The Process)

To the Component 8), the Components 2), 3) and 6) are added and dissolved. Then, the Component 1) is added and dissolved with heating, and then the Component 5) was dispersed. To this mixture, the Components 4) and 7) are added and dissolved with stirring.

| Blending example 7 Stick foundation | |
|---|---|
| (Prescription) | % by weight |
| 1) Titanium dioxide | 13.0 |
| 2) Kaolin | 12.0 |
| 3) Zinc oxide-covering talc | 13.7 |
| 4) Red iron oxide | 1.0 |
| 5) Yellow iron oxide | 0.7 |
| 6) Black iron oxide | 0.1 |
| 7) Squalane | 37.0 |
| 8) Cetyl 2-ethylhexanoate | 16.0 |
| 9) Sorbitan sesquioleate | 1.0 |
| 10) Microcrystalline wax | 4.0 |
| 11) Carnauba wax | 1.3 |
| 12) Perfume | 0.2 |

(The Process)

The Components 7) to 9) are mixed at 80° C., combined with the Components 1) to 6), mixed using a disper and subjected to a TK milling. To this mixture, the Components 10) and 11) which have been heated and dissolved are added, mixed and degassed. The Component 12) is mixed gently, and the mixture is charged at 80° C. into a container and then cooled.

| Blending example 8 Solid powder foundation | |
|---|---|
| (Prescription) | % by weight |
| 1) Sericite | 22.0 |
| 2) Synthesis mica | 15.0 |
| 3) Talc | remainder |
| 4) Zinc oxide-covering silica | 7.0 |
| 5) Ferric oxide | 0.8 |
| 6) Yellow iron oxide | 2.0 |
| 7) Black iron oxide | 0.1 |
| 8) Silicone elastic powder | 2.0 |
| 9) Spherical polyethylene | 4.0 |
| 10) Dimethylpolysiloxane | 3.0 |
| 11) Liquid paraffin | 5.0 |
| 12) Vaseline | 5.0 |
| 13) Sorbitan sesquiisostearate | 1.0 |
| 14) Paraben | proper quantity |
| 15) Antioxidant | proper quantity |
| 16) Perfume | proper quantity |

(The Process)

The Components 1) to 17) are stirred and mixed thoroughly using a blender

| Blending example 9 W/O type emulsified make-up base | |
|---|---|
| (Prescription) | % by weight |
| 1) Cyclomethycone | 30.0 |
| 2) Dimethycone | 2.0 |
| 3) Silicone resin | 1.0 |
| 4) Antioxidant | proper quantity |
| 5) Octyl methoxy cinnamate | 3.0 |
| 6) 4-tert-Buthyl-4'-methoxy benzoyl methane | 1.0 |
| 7) Isostearic acid | 1.0 |
| 8) Silicone treated alumina | 8.0 |
| 9) Cation modified bentonite | 2.0 |
| 10) Zinc oxide-covering talc | 5.0 |
| 11) Talc | 5.0 |
| 12) Spherical PMMA resin powder | 5.0 |
| 13) Purified water | remainder |
| 14) Glycerin | 4.0 |
| 15) Polyethylene glycol | 1.0 |

Blending example 9 W/O type emulsified make-up base

| (Prescription) | % by weight |
|---|---|
| 16) Antiseptics | proper quantity |
| 17) Stabilization agent | proper quantity |
| 18) Perfume | proper quantity |

(The Process)

The Components 1) to 9), 12), 16) to 18) are dissolved with heating at 85° C., combined with the Components 10) and 11), and dispersed (oil phase). To the Component 13), the Components 14) and 15) are added and dispersed uniformly (water phase). The oil phase is added to the water phase, kept at 85° C. for 100 minutes with stirring, cooled with stirring to 45° C.

Blending example 10 W/O emulsion type foundation

| 1) Silicone treated synthesis mica | 15.0 |
|---|---|
| 2) Silicone treated sericite | 7.0 |
| 3) Silicone treated titanium oxide | 12.0 |
| 4) Silicone treated ferric oxide | 1.2 |
| 5) Silicone treated yellow iron oxide | 2.3 |
| 6) Silicone treated black iron oxide | 0.6 |
| 7) Zinc oxide-covering mica | 12.0 |
| 8) Spherical polymethyl methacrylate powder | 4.0 |
| 9) Cyclomethycone | remainder |
| 10) Dimethylpolysiloxane | 4.0 |
| 11) Squalane | 3.0 |
| 12) Polyether modified silicone | 2.0 |
| 13) Sorbitan sesqiisostearate | 1.0 |
| 14) Dispersion auxiliary | proper quantity |
| 15) Dipropylene glycol | 2.0 |
| 16) Purified water | 20.0 |
| 17) Paraben | proper quantity |
| 18) Antioxidant | proper quantity |
| 19) Perfume | proper quantity |

(The Process)

The Components 1) to 14) are dissolved with heating at 85° C. (oil phase). To the Component 16), the Component 15) is added and dispersed uniformly (water phase). The oil phase is added to the water phase, kept at 85° C. for 100 minutes with stirring, combined with the Components 17) to 19), and cooled with stirring to 45° C.

The blending example 11 White powder

| 1) Talc | remainder |
|---|---|
| 2) Synthesis mica | 22.0 |
| 3) Zinc oxide-covering talc | 13.0 |
| 4) Spherical silicone powder | 4.0 |
| 5) Squalane | 3.0 |
| 6) Paraben | proper quantity |
| 7) Perfume | proper quantity |

(The Process)

The Components 1) to 6) are stirred and mixed thoroughly using a blender while spraying the Component 7) uniformly.

Blending example 12 O/W emulsion type foundation

| 1) Sericite | 17.0 |
|---|---|
| 2) Mica | 20.0 |
| 3) Zinc oxide-covering mica | 8.0 |
| 4) Ferric oxide | 0.3 |
| 5) Yellow iron oxide | 1.2 |
| 6) Black iron oxide | 0.6 |
| 7) Spherical polyethylene powder | 6.0 |
| 8) Squalane | 10.0 |
| 9) Olive oil | 10.0 |
| 10) Stearic acid | 2.0 |
| 11) Glyceryl monostearate | 2.0 |
| 12) POE (40) sorbitan monostearate | 2.0 |
| 13) Glycerol | 5.0 |
| 14) Triethanolamine | 0.8 |
| 15) pH modifier | proper quantity |
| 16) Antiseptics | proper quantity |
| 17) Purified water | remainder |

(The Process)

The Components 1) to 12) are dissolved with heating at 85° C. (oil phase). To the Component 17), the Components 13) to 15) are added and dispersed uniformly (water phase). The oil phase is added to the water phase, kept at 85° C. for 100 minutes with stirring, combined with the Component 16), and cooled with stirring to 45° C.

Blending example 13 O/W emulsion type make-up base

| 1) Purified water | remainder |
|---|---|
| 2) Glycerin | 20.0 |
| 3) 1,2-Pentanediol | 3.0 |
| 4) 1,3-Butylene glycol | 1.0 |
| 5) Liquid paraffin | 7.5 |
| 6) Isostearic acid | 0.5 |
| 7) Ascorbic acid | 0.2 |
| 8) Matricaria extract | 0.1 |
| 9) Saxifrage extract | 0.3 |
| 10) di-2-Ethylhexyl phthalate | 0.3 |
| 11) Spherical silica | 4.0 |
| 12) Zinc oxide-covering talc | 5.0 |
| 13) Talc | 5.0 |
| 14) Stabilization agent | proper quantity |
| 15) Perfume | proper quantity |

(The Process)

The Components 5) to 14) are dissolved with heating at 85° C. (oil phase). To the Component 1), the Components 2) to 4) are added and dispersed uniformly (water phase). The oil phase is added to the water phase, kept at 85° C. for 100 minutes with stirring, combined with the Component 15), and cooled with stirring to 45° C.

Blending example 14 Oil type eye shadow

| 1) Dimethicone | 10.0 |
|---|---|
| 2) Ester oil | 10.0 |
| 3) Liquid paraffin | remainder |
| 4) Squalane | 10.0 |
| 5) Sorbitan sesqiisostearate | 1.0 |
| 6) Polyethylene wax | 8.0 |
| 7) Ceresin wax | 3.0 |
| 8) Mica | 7.0 |
| 9) Spherical cellulose powder | 5.0 |
| 10) Mica titanium | 8.0 |
| 11) Zinc oxide-covering silica | 7.0 |
| 12) Kaolin | 10.0 |
| 13) Antioxidant | proper quantity |
| 14) Perfume | proper quantity |

(The Process)

The Components 1) to 7) are dissolved with heating at 85° C., combined with the Components 8) to 12), mixed with stirring, and then combined with the Components 13] and 14] with stirring, charged into a container, and then cooled.

| Blending example 15 Lipstick | | |
| --- | --- | --- |
| 1) | Polyethylene wax | 10.0 |
| 2) | Ceresin wax | 3.0 |
| 3) | Lanolin | 20.0 |
| 4) | Polybutene | 20.0 |
| 5) | Octylmethoxycinnamate | 5.0 |
| 6) | Dimethicone | 12.0 |
| 7) | Ester oil | remainder |
| 8) | Titanium oxide | 4.5 |
| 9) | Red number 201 | 0.5 |
| 10) | Red number 202 | 1.1 |
| 11) | Red number 223 | 0.3 |
| 12) | Spherical polyethylene powder | 3.0 |
| 13) | Ferric oxide-covering mica titanium | 12.0 |
| 14) | Zinc oxide-covering talc | 5.0 |
| 15) | Boron nitride powder | 5.0 |
| 16) | Antioxidant | proper quantity |
| 17) | Perfume | proper quantity |

(The Process)

The Components 1) to 7) are heated and dissolved at 85° C., combined with the Components 8) to 15), stirred and mixed and then combined with the Components 16) and 17) with stirring, charged into a container and cooled.

| Blending example 16 Two-way powder foundation | | |
| --- | --- | --- |
| 1) | Silicone treated sericite | 13.0 |
| 2) | Silicone treated mica | remainder |
| 3) | Silicone treated talc | 15.0 |
| 4) | Zinc oxide-covering mica | 5.0 |
| 5) | Aluminum Stearate treated microparticle titanium oxide | 6.0 |
| 6) | Silicone treated titanium oxide | 9.0 |
| 7) | Silicone treated ferric oxide | 1.2 |
| 8) | Silicone treated yellow iron oxide | 2.5 |
| 9) | Silicone treated black iron oxide | 0.9 |
| 10) | Barium sulfate powder | 7.0 |
| 11) | Polyurethane powder | 1.0 |
| 12) | Silicone elastic powder | 5.0 |
| 13) | Polyethylene powder | 2.0 |
| 14) | Mica titanium | 4.0 |
| 15) | Paraben | proper quantity |
| 16) | Dimethylpolysiloxane | 3.0 |
| 17) | Methyl phenyl polysiloxane | 2.0 |
| 18) | Vaseline | 2.0 |
| 19) | Octylmethoxycinnamate | 3.0 |
| 20) | Sorbitan sesqiisostearate | 1.0 |
| 21) | Polyether silicone | 1.0 |
| 22) | Antioxidant | proper quantity |
| 23) | Perfume | proper quantity |

(The Process)

The Components 1) to 22) are heated and dissolved at 85° C., and then spraying the Component 23) uniformly.

| Blending example 17 Two-way powder foundation | | |
| --- | --- | --- |
| 1) | Silicone treated sericite | 22.0 |
| 2) | Silicone treated mica | remainder |
| 3) | Silicone treated kaolin | 10.0 |
| 4) | Zinc oxide-covering silica | 7.0 |
| 5) | Silicone treated microparticle titanium oxide | 8.0 |
| 6) | Silicone treated titanium oxide | 9.0 |
| 7) | Silicone treated ferric oxide | 1.2 |
| 8) | Silicone treated yellow iron oxide | 2.5 |
| 9) | Silicone treated black iron oxide | 0.9 |
| 10) | Spherical silicone powder | 8.0 |
| 11) | Lauroyl lysine membrane titanium oxide | 4.0 |
| 12) | Paraben | proper quantity |
| 13) | Dimethylpolysiloxane | 4.0 |
| 14) | Polyethylene glycol | 2.0 |
| 15) | Fluoro polyether | 2.0 |
| 16) | Octylmethoxycinnamate | 2.0 |
| 17) | Sorbitan sesqiisostearate | 1.0 |
| 18) | Antioxidant | proper quantity |
| 19) | Perfume | proper quantity |

(The Process)

The Components 1) to 18) are heated and dissolved at 85° C., and then spraying the Component 19) uniformly.

| Blending example 18 Wiping off preparation for cleaning | |
| --- | --- |
| 1) Purified water | 91.945 |
| 2) Sodium chloride | 0.35 |
| 3) Dipropylene glycol | 2.0 |
| 4) Sodium hexa-metaphosphate | 0.005 |
| 5) Zinc oxide-covering talc | 5.0 |
| 6) Bentonite | 0.5 |
| 7) Methyl paraben | 0.1 |
| 8) POE (20) octyl dodecyl ether | 0.1 |

(The Process)

The Components 2) to 8) are dissolved and dispersed in the Compound 1) with stirring thoroughly, and an unwoven fabric is impregnated with this mixture.

| Blending example 19 Paper powder | |
| --- | --- |
| 1) Colorant | 25 |
| 2) Zinc oxide-covering silica | 3 |
| 3) Carboxymethylcellulose sodium | 0.2 |
| 4) Sodium dehydroacetate | 0.1 |
| 5) Sodium metaphosphate | 0.2 |
| 6) Polyoxyethylene sorbitan monooleate (20 E.O.) | 0.2 |
| 7) Perfume | 0.1 |
| 8) Purified water | proper quantity |
| Total | 100 |

(The Process)

The coating solution that mixed the Components 1) to 7) in the Components 8) is coated on the paper, and dried.

Any of the external compositions of the Blending examples 1 to 19 had a plasminogen activator adsorbing effect and inhibiting effect, and exhibits excellent improving effect and preventing effects against rough skin or pimples experienced by a normal human as well as contact dermatitis, psoriasis, atopic dermatitis.

As described above, a complex powder of the present invention has abilities of adsorbing and operating on a specific enzyme, and said complex powder is highly safe and exhibits excellent effect to the skin.

What is claimed is:

1. A method of improving the condition of rough skin, which condition accompanies an activity change for a plasminogen activator, comprising
applying to rough skin an external composition including a complex powder, the complex powder comprising:
an adsorption site comprising a material selected from the group consisting of silica, talc, mica, polymethyl methacrylate, silicone resin and combinations thereof and
an operation site, including zinc oxide,
wherein said adsorption site attracts or adsorbs a plasminogen activator,
wherein said operation site inhibits said plasminogen activator,
and wherein said adsorption site and said operation site are present on the surface of the complex powder,
wherein the operation site takes the form of stripes or spots on the surface of the adsorption site, and
wherein 2 to 70% of the surface area of the adsorption site is covered by the operation site.

2. The method of claim 1, wherein 1 to 70 wt % of the operation site covers the adsorption site, based on the weight of the adsorption site.

3. The method of claim 1, wherein 4 to 50% of the surface area of the adsorption site is covered by the operation site.

4. A method of improving the condition of rough skin, which condition accompanies an activity change for a plasminogen activator, comprising:
applying to skin an external composition including a complex powder, the complex powder comprising
an adsorption site comprising a material selected from the group consisting of talc, mica, polyamide, polymethyl methacrylate, silicone resin and combinations thereof and
an operation site, including zinc oxide,
wherein said adsorption site attracts or adsorbs a plasminogen activator,
wherein said operation site inhibits said plasminogen activator,
wherein said adsorption site and said operation site are present on the surface of the complex powder,
wherein the adsorption site has a form selected from the group consisting of stripes, spots, or combinations thereof, the adsorption site being situated on the surface of the operation site,
wherein 0.1 to 75 wt % of the adsorption site covers the operation site, based on the weight of the operation site.

5. The method of claim 4, wherein 3 to 50 wt % of the adsorption site covers the operation site, based on the weight of the operation site.

6. The method of claim 4, wherein the metal ion elution level during use is 0.7 to 40 ppm.

7. The method of claim 4, wherein the metal ion elution level during use is 1.2 to 30 ppm.

8. A method of improving the condition of rough skin, which condition accompanies an activity change for a plasminogen activator, comprising:
applying to skin an external composition including a complex powder, the complex powder comprising:
an adsorption site comprising a material selected from the group consisting of silica, talc, mica, polyamide, polymethyl methacrylate, silicone resin and combinations thereof,
an operation site, including zinc oxide and a substrate particle, and
a substrate particle
wherein said adsorption site attracts or adsorbs a plasminogen activator,
wherein said operation site inhibits said plasminogen activator,
wherein said adsorption site and said operation site are present on the surface of the complex powder,
wherein 2 to 70% of the surface area of the adsorption site is covered by the operation site, and
wherein the adsorption site with the operation site takes the form of stripes or spots on the surface of the substrate particle.

9. The method of claim 1, wherein the relationship between $\zeta$-potential and zinc ion elution level is represented by $$\zeta\text{-potential (mV)} \leq \text{Zinc ion elution level (ppm)} \times 1.5 - 25.$$

10. The method of claim 1, wherein the plasminogen activator is urokinase.

11. The method of claim 1, wherein the operation site is zinc oxide.

12. The method of claim 11, wherein the plasminogen activator is urokinase.

13. The method of claim 4, wherein the relationship between $\zeta$-potential and zinc ion elution level is represented by $$\zeta\text{-potential (mV)} \leq 5 \text{ Zinc ion elution level (ppm)} \times 1.5 - 25.$$

14. The method of claim 4, wherein the plasminogen activator is urokinase.

15. The method of claim 4, wherein the operation site is zinc oxide.

16. The method of claim 15, wherein the plasminogen activator is urokinase.

17. The method of claim 8, wherein the plasminogen activator is urokinase.

18. The method of claim 8, wherein the operation site is zinc oxide.

19. The method of claim 18, wherein the plasminogen activator is urokinase.

* * * * *